United States Patent
Fujikado et al.

(10) Patent No.: US 11,363,948 B2
(45) Date of Patent: Jun. 21, 2022

(54) OPHTHALMOLOGIC DEVICE AND METHOD OF OPERATING OPHTHALMOLOGIC DEVICE

(71) Applicants: OSAKA UNIVERSITY, Suita (JP); TOPCON CORPORATION, Tokyo (JP)

(72) Inventors: Takashi Fujikado, Suita (JP); Yoko Hirohara, Itabashi-ku (JP); Makoto Saika, Itabashi-ku (JP); Suguru Miyagawa, Itabashi-ku (JP)

(73) Assignees: OSAKA UNIVERSITY, Osaka (JP); TOPCON CORPORATION, Tokyo (JP)

(*) Notice: Subject to any disclaimer, the term of this patent is extended or adjusted under 35 U.S.C. 154(b) by 290 days.

(21) Appl. No.: 16/691,882

(22) Filed: Nov. 22, 2019

(65) Prior Publication Data

US 2020/0085293 A1 Mar. 19, 2020

Related U.S. Application Data

(63) Continuation of application No. PCT/JP2018/018729, filed on May 15, 2018.

(30) Foreign Application Priority Data

May 24, 2017 (JP) .............................. JP2017-102463

(51) Int. Cl.
*A61B 3/103* (2006.01)
*A61B 3/00* (2006.01)
(Continued)

(52) U.S. Cl.
CPC ............ *A61B 3/103* (2013.01); *A61B 3/0025* (2013.01); *A61B 3/0041* (2013.01);
(Continued)

(58) Field of Classification Search
CPC ..... A61B 3/103; A61B 3/0025; A61B 3/0041; A61B 3/0091; A61B 3/1015; A61B 3/1035; A61B 3/18; A61B 3/09
(Continued)

(56) References Cited

U.S. PATENT DOCUMENTS

| | | | | |
|---|---|---|---|---|
| 5,815,240 A | * | 9/1998 | Iki | A61B 3/107 351/205 |
| 5,828,439 A | * | 10/1998 | Ueno | A61B 3/103 351/205 |

(Continued)

FOREIGN PATENT DOCUMENTS

| | | |
|---|---|---|
| JP | 2008-534051 A | 8/2008 |
| JP | 2010-110388 A | 5/2010 |

(Continued)

OTHER PUBLICATIONS

International Preliminary Report on Patentability (IPRP) dated Nov. 26, 2019, issued in corresponding International Application No. PCT/JP2018/018729.

(Continued)

*Primary Examiner* — Mohammed A Hasan
(74) *Attorney, Agent, or Firm* — Xsensus LLP

(57) ABSTRACT

An ophthalmologic device includes: a visual target presenting unit configured to present a common visual target to be viewed with both subject's eyes; a presenting distance changing unit configured to change a presenting distance of the visual target presented by the visual target presenting unit from a predetermined far vision distance to a predetermined near vision distance; an ocular characteristic acquiring unit configured to objectively acquire an optical characteristic of the subject's eyes; an addition power adding unit configured to add the addition power to the both subject's eyes; and a control unit configured to cause the presenting distance changing unit to change the presenting (Continued)

distance and the ocular characteristic acquiring unit to continuously acquire the optical characteristic, in a state in which an addition power is added to the both subject's eyes by the addition power adding unit.

15 Claims, 22 Drawing Sheets

(51) Int. Cl.
  *A61B 3/10* (2006.01)
  *A61B 3/18* (2006.01)
(52) U.S. Cl.
  CPC .......... *A61B 3/0091* (2013.01); *A61B 3/1015* (2013.01); *A61B 3/1035* (2013.01); *A61B 3/18* (2013.01)
(58) Field of Classification Search
  USPC ....................................................... 351/216
  See application file for complete search history.

(56) References Cited

U.S. PATENT DOCUMENTS

| 7,370,964 | B2* | 5/2008 | Wakil | A61B 3/0091 |
| | | | | 351/203 |
| 2004/0218142 | A1 | 11/2004 | Wakil et al. | |
| 2011/0187996 | A1 | 8/2011 | Ueno et al. | |
| 2014/0211165 | A1* | 7/2014 | Kobayashi | A61B 3/032 |
| | | | | 351/237 |
| 2019/0090736 | A1* | 3/2019 | Nakajima | A61B 3/112 |

FOREIGN PATENT DOCUMENTS

| JP | 2011-156291 A | 8/2011 | | |
| JP | 2011-194271 A | 10/2011 | | |
| JP | 2014-045924 A | 3/2014 | | |
| JP | 2014-147416 A | 8/2014 | | |
| JP | 2015-012963 A | 1/2015 | | |
| WO | 03/009746 A1 | 2/2003 | | |
| WO | 2006/101656 A2 | 9/2006 | | |
| WO | WO-2006101656 A2 * | 9/2006 | ............... | A61B 3/11 |
| WO | 2006/124380 A2 | 11/2006 | | |
| WO | 2017/002846 A1 | 5/2018 | | |

OTHER PUBLICATIONS

Extended European Search Report dated May 4, 2020 in European Application No. 18805566.9.
Office Action dated Feb. 1, 2022, in corresponding Japanese patent Application No. 2019-519590, 6 pages.

* cited by examiner

FIG.12 <THIRD SUBJECT (LATE 40'S)>

FIG.19
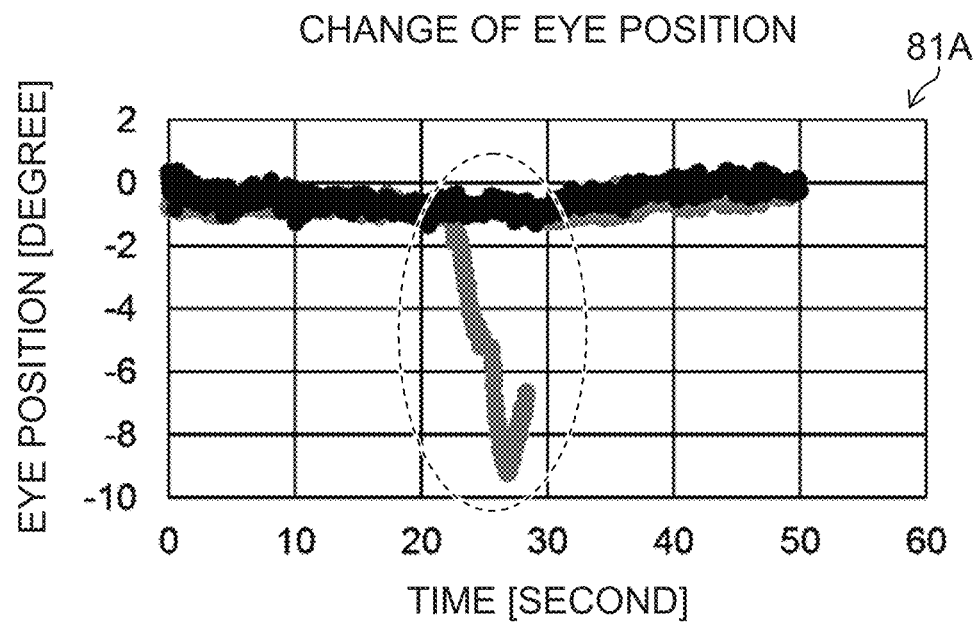
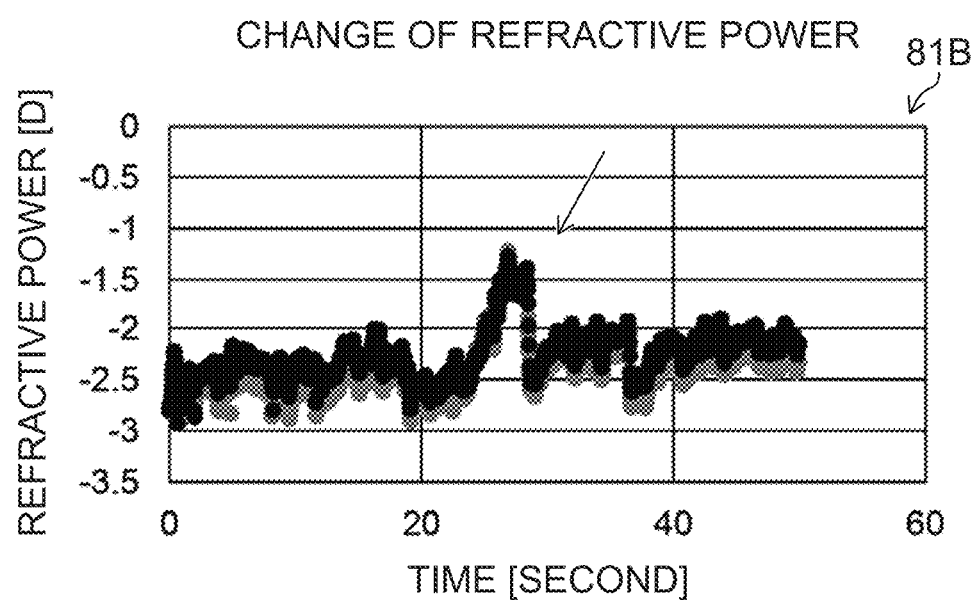

OPHTHALMOLOGIC DEVICE AND METHOD OF OPERATING OPHTHALMOLOGIC DEVICE

CROSS-REFERENCE TO RELATED APPLICATIONS

The present application is a Bypass Continuation of PCT International Application No. PCT/JP2018/018729, filed on May 15, 2018 claiming priority under 35 U.S.C § 119(a) to Japanese Patent Application No. 2017-102463, filed on May 24, 2017. Each of the above applications is hereby expressly incorporated by reference, in its entirety, into the present application.

BACKGROUND OF THE INVENTION

1. Field of the Invention

The present invention relates to an ophthalmologic device suitable for manufacturing spectacle lenses and to a method of operating the ophthalmologic device.

2. Description of the Related Art

Particularly, middle-aged and elderly people often use spectacles for near vision when performing near work because the function of accommodative response, that is, the function of focus position accommodation is reduced due to presbyopia (aged eye) that occurs with age. The spectacle lens for such spectacles for near vision is usually prescribed (near vision prescription) relying on the experience of the examiner, and the examiner empirically determines addition powers of the spectacle lenses according to the age of the subject. Therefore, there are problems that it takes long time for near vision prescription and individual difference may occur depending on examiners. Thus, it is desirable to automate the determination of especially suitable addition power among the near vision prescriptions.

Patent Literature 1 discloses an ocular refractive power measuring apparatus configured to move a visual target to a preset near distance to present the visual target, then compare a first spherical power required for a subject's eye to see the visual target moved to the near distance and a second spherical power of the subject's eye obtained by objective ocular refractive power measurement for near vision, and obtain a required addition power from the difference between the first spherical power and the second spherical power. In addition, the ocular refractive power measuring apparatus adds the obtained addition power to the subject's eye, finely adjusts the addition power, and then measures a limit (threshold) of near vision power of the subject's eye.

Patent Literature 2 discloses an optometry apparatus configured to measure a refractive power of a subject's eye continuously for a fixed time in a state in which a visual target is presented at an arbitrary near distance, analyze data on temporal change obtained by the measurement, and determine the presence or absence of a tension state based on a frequency of appearance of a frequency component indicating a ciliary body tonic micromotion obtained from the result of analysis, thereby obtaining an adequate addition power without excessive tension. With this optometry apparatus, it becomes possible to manufacture spectacle lenses for near vision which provide less eye fatigue in a near vision for a long time.

CITATION LIST

Patent Literature 1: Japanese Patent Application Laid-Open No. 2010-110388

Patent Literature 2: Japanese Patent Application Laid-Open No. 2011-156291

SUMMARY OF THE INVENTION

When the spectacle lenses for near vision spectacles are manufactured by performing determination and prescription of the addition power of the spectacle lenses based on the limit of accommodative amplitude (amplitude of accommodation) of the subject's eyes obtained by the ocular refractive power measuring apparatus of Patent Literature 1, there arises a problem that the eyes tend to become fatigued if the spectacles for near vision are worn for a long period of time. Therefore, it is still necessary to adjust the addition power based on the examiner's experience.

In contrast, with the optometry apparatus of Patent Literature 2, manufacture of the spectacle lens for near vision, which provides less eye fatigue in near vision for a long time as described above is enabled. However, both of the apparatuses of Patent Literature 1 and Patent Literature 2 are configured to perform measurement for each eye by presenting visual targets aligned in the apparatus to the subject's eye. Consequently, in the apparatuses disclosed in Patent Literature 1 and Patent Literature 2, when the presenting position of the visual targets is changed to a distance for near vision (near vision distance), measurement is performed in a state in which the subject's eye is constantly fixed to view front (a state in which eye positions are not changed). It is known that the convergence of both eyes occurs when a person looks at a nearby object in a natural state, and the accommodation (convergence accommodation) is induced by this convergence. Therefore, when the accommodative amplitude still remains in the subject's eyes, near viewing may be achieved by the convergence accommodation. Therefore, it is difficult to say that the above-described measurement without the convergence stimulation is reproducing the condition of the natural vision, and thus the above-described measurement is not sufficient for determination of the addition power.

In view of such circumstances, it is an object of the present invention to provide an ophthalmologic device and a method of operating an ophthalmologic device, which are used to determine the optimal addition power which is closer to the natural vision state.

In order to achieve the above-described object, an ophthalmologic device includes: a visual target presenting unit configured to present a common visual target to be viewed with both subject's eyes; a presenting distance changing unit configured to change a presenting distance of the visual target presented by the visual target presenting unit from a predetermined far vision distance to a predetermined near vision distance; an ocular characteristic acquiring unit configured to objectively acquire an optical characteristic of the subject's eyes; an addition power adding unit configured to add the addition power to the both subject's eyes; and a control unit configured to cause the presenting distance changing unit to change the presenting distance and the ocular characteristic acquiring unit to continuously acquire the optical characteristic, in a state in which an arbitrary addition power is added to the both subject's eyes by the addition power adding unit.

According to the ophthalmologic device, it is possible to present the visual target at the near vision distance considering convergence of the both subject's eyes, and measure the optical characteristic of the both eyes with accommodative change induced by convergence included. Consequently, it is possible to obtain the optical characteristic of both subject's eyes used for determining optimal addition power which is closer to natural vision state.

In the ophthalmologic device according to another aspect of the present invention, the control unit causes an ocular characteristic acquiring unit to acquire a change in optical characteristic for a fixed time before and after the presenting distance is changed by the presenting distance changing unit. Accordingly, it is possible to measure the optical characteristic of the both eyes with the accommodative change induced by convergence included.

In the ophthalmologic device according to another aspect of the present invention, the addition power adding unit changes the addition power to be added to both eyes, and the control unit performs repeating control that causes the presenting distance changing unit to change the presenting distance and causes the ocular characteristic acquiring unit to continuously acquire optical characteristics every time when the addition powers to be added to both eyes by the addition power adding unit are changed. Accordingly, the optical characteristics of both subject's eyes used for determining optimal addition power closer to natural vision state is obtained.

The ophthalmologic device according to another aspect of the present invention includes an addition power determining unit configured to determine the addition power suitable to the both eyes based on a result of acquisition of the optical characteristic acquired by the ocular characteristic acquiring unit for each addition power, by the repeating control. Accordingly, it is possible to determine an optimal addition power which is closer to the natural vision state.

The ophthalmologic device according to another aspect of the present invention includes an accommodative amplitude judging unit configured to judge an accommodative amplitude of the subject's eyes based on the optical characteristic acquired by the ocular characteristic acquiring unit, and when the accommodative amplitude judged by the accommodative amplitude judging unit satisfies a predetermined accommodative amplitude criteria, the addition power determining unit determines the addition power based on judgment result of value and fluctuation of the optical characteristic for each addition power, which have been acquired by the ocular characteristic acquiring unit. Accordingly, it is possible to determine an optimal addition power which is closer to the natural vision state.

The ophthalmologic device according to another aspect of the present invention includes an accommodative amplitude judging unit configured to judge an accommodative amplitude of the subject's eyes based on the optical characteristics acquired by the ocular characteristic acquiring unit, and when the accommodative amplitude judged by the accommodative amplitude judging unit does not satisfy a predetermined accommodative amplitude criteria and when the optical characteristic acquired by the ocular characteristic acquiring unit shows a return of the optical characteristic indicating that the optical characteristic gets closer according to the elapse of the time, to a value before the presenting distance is changed, the addition power determining unit determines the addition power based on judgment result of a magnitude of the return for each addition power. Accordingly, when both subject's eyes still have the accommodative amplitude, it is possible to determine an optimal addition power for the subject's eyes.

In the ophthalmologic device according to another aspect of the present invention, the addition power adding unit determines addition powers to be added to the both subject's eyes in the repeating control, based on the optical characteristic acquired by the ocular characteristic acquiring unit in a state in which no addition power is added to the both subject's eyes. Accordingly, it is possible to decrease time required for determining the optimal addition power for subject's eyes.

The ophthalmologic device according to another aspect of the present invention includes a fully corrected state confirming unit configured to objectively confirm a fully corrected state of the both subject's eyes based on the optical characteristic acquired by the ocular characteristic acquiring unit when the presenting distance is the far vision distance.

In the ophthalmologic device according to another aspect of the present invention, the ocular characteristic acquiring unit acquires a spherical equivalent power as the optical characteristic.

In the ophthalmologic device according to another aspect of the present invention, the ocular characteristic acquiring unit acquires the optical characteristic and convergence angles of the both subject's eyes. Accordingly, it is possible to judge whether or not the natural vision state in which the both subject's eyes view the visual target naturally is reproduced in measurement for each addition power, based on the convergence angle acquired for each addition power.

In the ophthalmologic device according to another aspect of the present invention, the ocular characteristic acquiring unit includes: a pair of optical members individually provided for optical paths connecting the both subject's eyes and the visual target; and a pair of wave-front sensors provided respectively at positions shifted in the vertical direction with respect to the optical paths from positions of the optical members, the pair of wave-front sensors configured to respectively emit measuring lights toward the optical members facing the wave-front sensors, wherein the pair of optical members respectively transmit image lights of the visual target, reflect measuring lights entering from the wave-front sensors to the subject's eyes facing the optical members, and reflect the measuring lights reflected from the subject's eyes toward the wave-front sensors facing the optical members, the pair of wave-front sensors respectively receive the measuring lights entering from the optical members facing the wave-front sensors and output light receiving signals, and the ocular characteristic acquiring unit acquires the optical characteristic based on the light receiving signals output from the wave-front sensors. Accordingly, it is possible to obtain the optical characteristic of the both subject's eyes used for determining an optimal addition power which is closer to natural vision state.

A method of operating the ophthalmologic device for achieving the object of the present invention includes: a visual target presenting step of presenting a common visual target to be viewed with both subject's eyes; a presenting distance changing step of changing a presenting distance of the visual target presented in the visual target presenting step from a predetermined far vision distance to a predetermined near vision distance; an ocular characteristic acquiring step of objectively acquiring an optical characteristic of the subject's eyes; an addition power adding step of adding the addition power to the both subject's eyes; and a controlling step of performing the change of the presenting distance by the presenting distance changing step and the continuous acquisition of the optical characteristic by the ocular characteristic acquiring step, in a state in which the addition power is added to the both subject's eyes in the addition power adding step.

In the method of operating an ophthalmologic device according to another aspect of the present invention, the addition power to be added to both eyes is changed in the addition power adding step, and the controlling step performs repeating control for repeatedly performing the change of the presenting distance by the presenting distance changing step and continuous acquisition of the optical characteristic by the ocular characteristic acquiring step, every time when the addition power to be added to the both subject's eyes is changed in the addition power adding step.

The method of operating an ophthalmologic device according to another aspect of the present invention includes an addition power determining step of determining the addition power suitable to the both subject's eyes based on a result of acquisition of the optical characteristic acquired for each addition power by the repeating control.

The method of operating an ophthalmologic device according to another aspect of the present invention includes a fully corrected state confirming step of objectively confirming a fully corrected state of the both subject's eyes based on the optical characteristic acquired in the ocular characteristic acquiring step when the presenting distance is the far vision distance.

The ophthalmologic device and the method of operating the ophthalmologic device of the present invention can be used for determining optimal addition power closer to the natural vision state.

BRIEF DESCRIPTION OF THE DRAWINGS

FIG. 19 is a graph showing an example of temporal change of eye positions and the refractive powers of the subject's eyes in a case of increasing the light intensity difference of the visible lights entering respectively into both subject's eyes having phoria-myopia.

DESCRIPTION OF EMBODIMENTS

<Ophthalmologic Device in First Embodiment>

Figure 1:
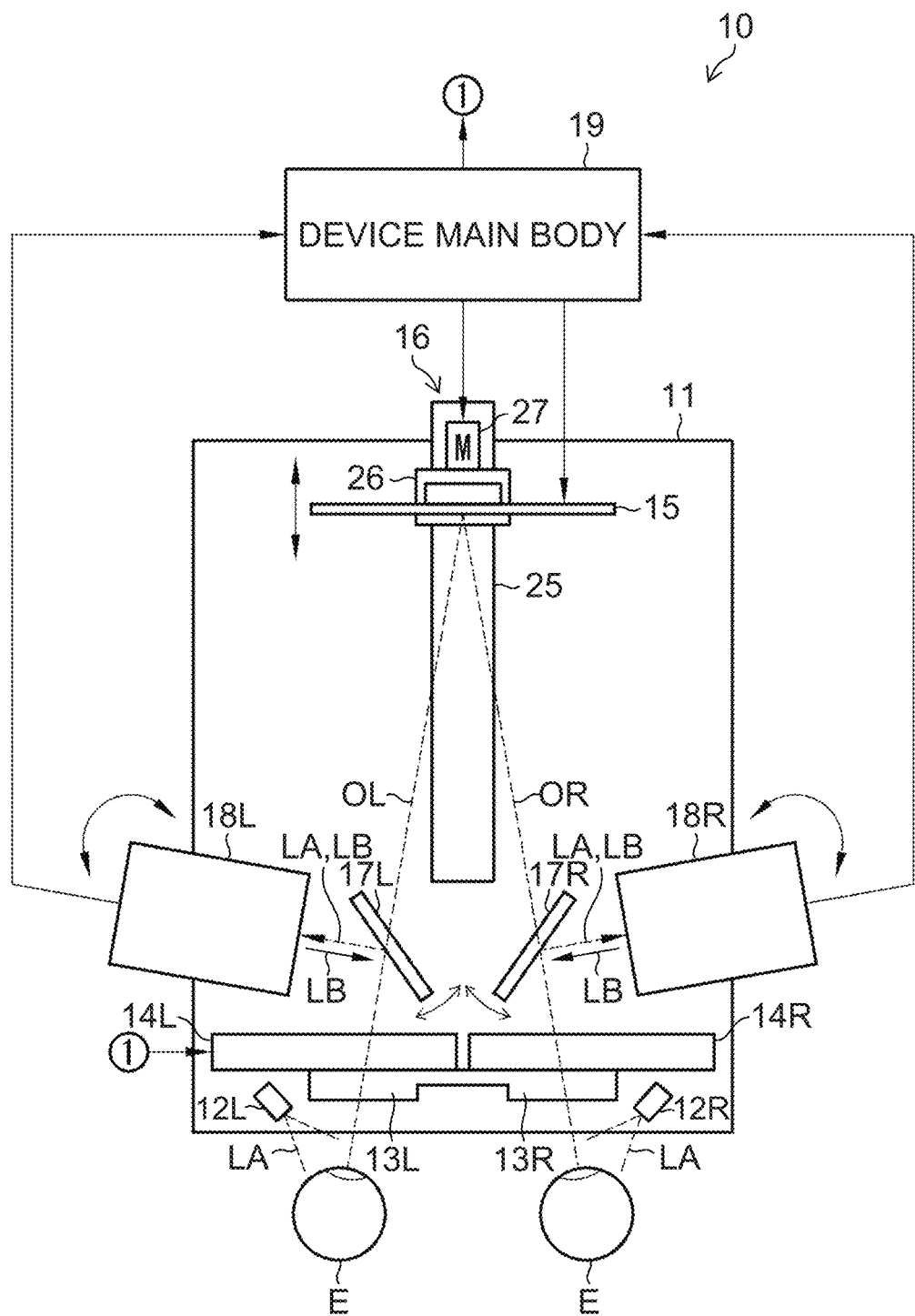
FIG. 1 is a schematic top view of an ophthalmologic device according to a first embodiment.

FIG. 1 is a schematic top view of an ophthalmologic device 10 according to a first embodiment. As illustrated in FIG. 1, the ophthalmologic device 10 acquires full correction values for both subject's eyes E of a subject and determines addition powers suitable for the both subject's eyes E. The full correction values and the addition powers obtained by the ophthalmologic device 10 are used for prescription of spectacle lenses for near vision (illustration is omitted), that is, for manufacturing the spectacle lens for near vision.

The ophthalmologic device 10 includes a table 11, a pair of infrared sources 12R, 12L, eyepieces 13R, 13L, addition power adding units 14R, 14L, a visual target presenting unit 15, a visual target moving mechanism 16, a pair of dichroic mirrors 17R, 17L, a pair of wave-front sensors 18R, 18L (also referred to as binocular wave-front sensor), and a device main body 19. The ophthalmologic device 10 may have a plurality of operation modes including a full correction value acquiring mode for acquiring (measuring) full correction values of subject's eyes E, and an addition power determining mode for determining addition powers suitable for the subject's eyes E.

Respective parts and units of the ophthalmologic device 10 are provided on the table 11. The table 11 includes a face supporting unit, not illustrated, on the front end portion located on the subject side (a lower end portion in the drawing). The face supporting unit supports one or both of a forehead and a chin of the subject to stabilize the positions of the subject's eyes E on the table 11.

The infrared sources 12R, 12L are mounted on a housing (not illustrated) disposed on substantially forward of the subject's eyes E. The infrared source 12R is mounted in the vicinity of a right eye of the subject's eyes E, and a near infrared light LA is emitted toward the right eye. Likewise, the infrared source 12L is mounted in the vicinity of a left eye of the subject's eyes E, and a near infrared light LA is emitted toward the left eye. A wavelength range of the near infrared light LA is, for example, 950 nm.

The eyepieces 13R, 13L are provided on the table 11 described above. The eyepiece 13R is provided at a position facing the right eye of the subject's eyes E. Accordingly, the right eye can view a visual target 28 (see FIG. 4), described later, through the eyepiece 13R. The eyepiece 13L is provided at a position facing the left eye of the subject's eyes E. Accordingly, the left eye can view the visual target 28 through the eyepiece 13L.

Figure 2:
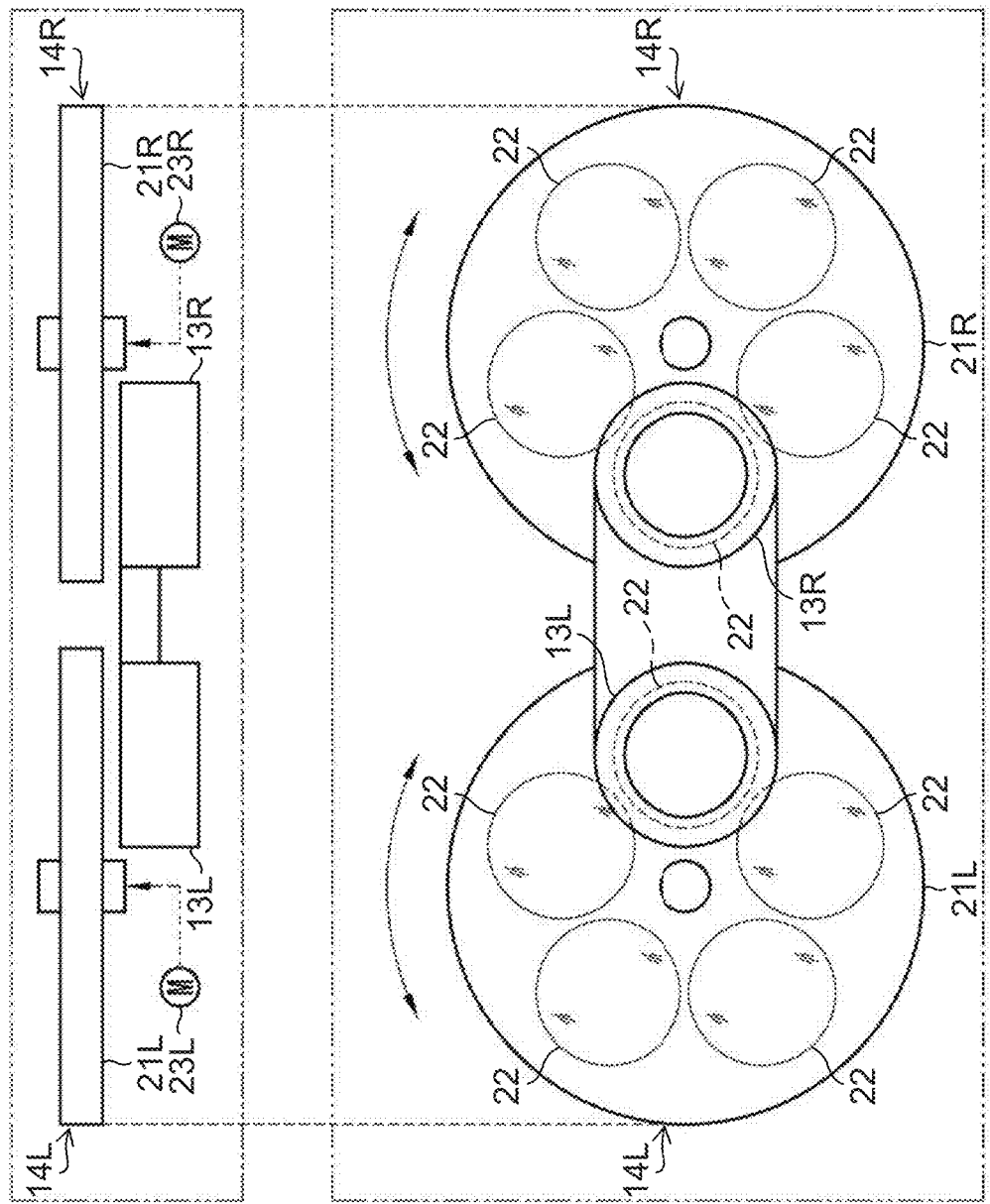
FIG. 2 illustrates a top view and a front view illustrating an example of an addition power adding unit.

FIG. 2 shows a top view (upper part) and a front view (lower part) illustrating an example of the addition power adding units 14R, 14L configured to add powers respectively to both subject's eyes E. As illustrated in FIG. 2, the addition power adding units 14R, 14L change the addition powers to be added to both subject's eyes E in the addition power determining mode. The addition power adding unit 14R includes a turret 21R provided on the front side (opposite side from the subject's eyes E) of the eyepiece 13R, five types of lenses 22 provided on the turret 21R, and a rotary driving unit 23R configured to rotationally driving the turret 21R.

The turret 21R is provided with the five types of lenses 22 on the same circumference. The turret 21R is rotationally driven by the rotary driving unit 23R, so that the five types of lenses 22 are selectively disposed on the front side of the eyepiece 13R. The five types of lenses 22 are added with addition powers of 0 D (Diopter), 0.5 D, 1.0 D, 1.5 D, and 2.0 D, respectively. Note that a portion of the turret 21R where the lens 22 of 0 D is provided may be a space. By rotationally driving the turret 21R by the rotary driving unit 23R, five types of addition powers may be added selectively to the right eye of the subject's eyes E. Note that it is desirable to provide the respective lenses 22 with an antireflection film or the like as antireflection means for near infrared light (wavelength range: approximately 800 nm to 1100 nm) for measurement in order to prevent reflected light from the lenses 22 from becoming noise in aberration measurement and observation of anterior eye part.

The rotary driving unit 23R includes a motor and a drive transmission mechanism. The rotary driving unit 23R, when being set to the addition power determining mode, changes the addition power to be added to the right eye of the subject's eyes E by rotating the turret 21R under the control of the device main body 19, described later. Specifically, the addition power to be added to the right eye is varied stepwise in the order of 0 D, 0.5 D, 1.0 D, 1.5 D, and 2.0 D. In the full correction value acquiring mode, the addition power to be added to the right eye is set to 0 D, that is, to a non-added state in which no addition power is added.

The addition power adding unit 14L includes a turret 21L provided on the front side of the eyepiece 13L, five types of lenses 22 provided on the turret 21L, and a rotary driving unit 23L configured to rotationally driving the turret 21L. As the configuration of each part of the addition power adding unit 14L is basically the same as the addition power adding unit 14R described above, specific description will be omitted here. The addition power adding unit 14L, when being set to the addition power determining mode, changes the addition power to be added to the left eye of the subject's eyes E stepwise in the order of 0 D, 0.5 D, 1.0 D, 1.5 D, and 2.0 D. Also, the addition power adding unit 14L, when being set to the full correction value acquiring mode, sets the power to be added to the left eye to 0 D, that is, to the non-added state.

Note that although the turrets 21R, 21L are rotationally driven respectively by the rotary driving units 23R, 23L in this embodiment, the turrets 21R, 21L may be rotated by a manual operation by the examiner. The addition power adding units 14R, 14L are not limited to the turret type, and may be of a test frame type, for example, and in this case, the examiner changes the addition power to be added to the subject's eyes E by replacing the lenses 22 by manual operation.

The addition power to be added to both subject's eyes E in the addition power determining mode is not limited to the five types of degrees described above. The number of types of degrees may be changed as needed. For example, a larger number of types of degrees may be provided so as to widen the range of the addition power or narrow intervals of the addition powers.

Returning back to FIG. 1, the table 11 has the visual target presenting unit 15 at a rear end side which is opposite to the front end side. A liquid crystal display is used as the visual target presenting unit 15 in this embodiment. The visual target presenting unit 15 presents the common (same) visual target 28 (see FIG. 4) to be viewed with both of the subject's eyes E. The visual target presenting unit 15 is retained by the visual target moving mechanism 16 so as to be freely movable in the front-rear direction (the direction toward the subject's eyes E and the direction away from the subject's eyes E) of the table 11.

The visual target moving mechanism 16 corresponds to the presenting distance changing unit of the present invention. The visual target moving mechanism 16 changes the presenting distance (see FIG. 4) at which the visual target 28 is presented to the subject's eyes E by the visual target presenting unit 15, that is, the distance between the visual target 28 and the subject's eyes E in a short time by moving the visual target presenting unit 15 in the front-rear direction of the table 11 at a high speed. The visual target moving mechanism 16 includes a guide rail 25 provided on an upper surface of the table 11 and extending in the front-rear direction, a supporting unit 26 slidably provided on the guide rail 25 and configured to support the visual target presenting unit 15, and a visual target moving unit 27 configured to move (displace) the supporting unit 26 along the guide rail 25.

The visual target moving unit 27 includes a motor and a drive transmission mechanism, and configured to set (adjust) the presenting distance of the visual target 28 (see FIG. 4) by moving the visual target presenting unit 15 in the front-rear direction at a high speed via the supporting unit 26 under the control of the device main body 19, described later.

Figure 3:
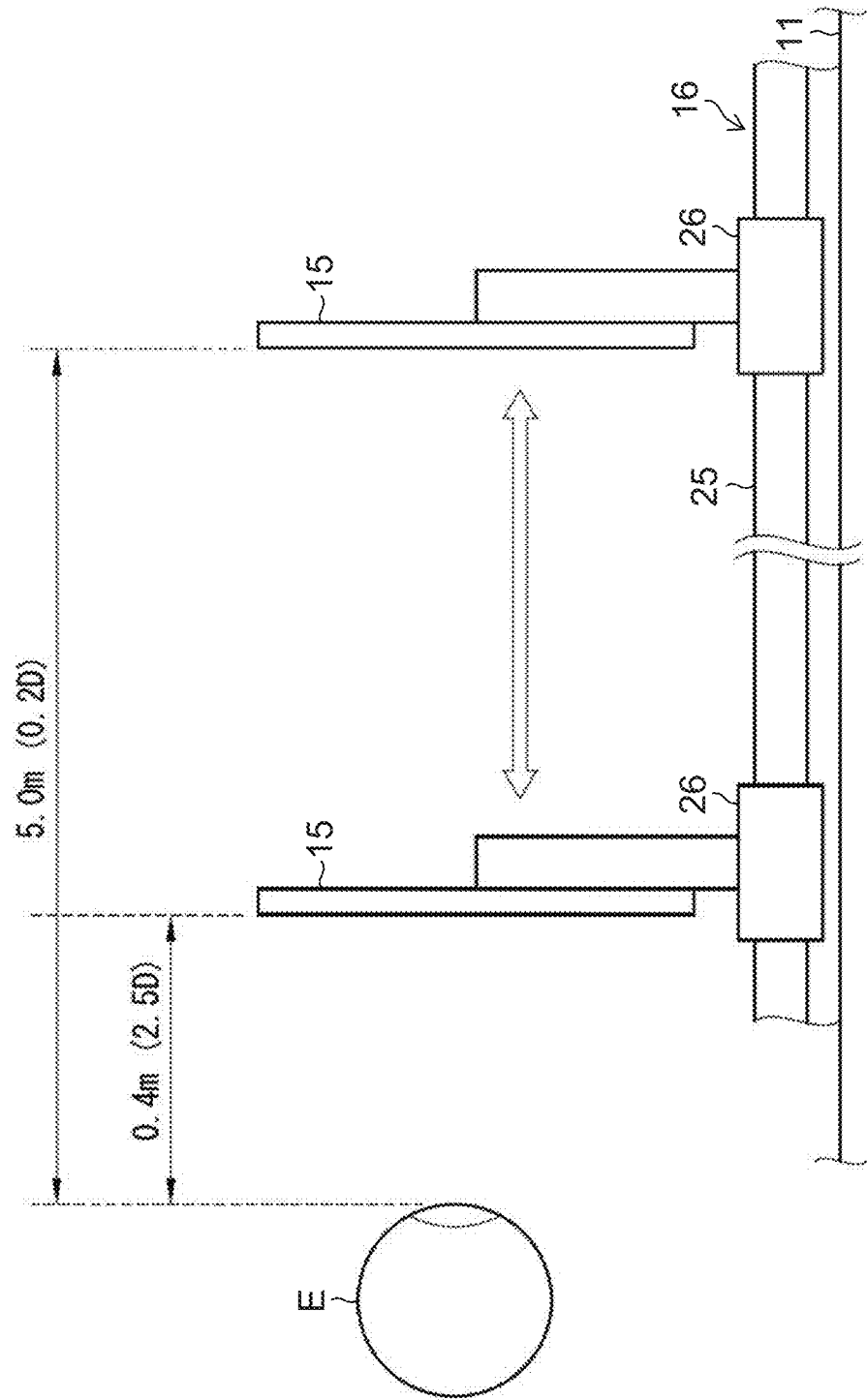
FIG. 3 is an explanatory drawing for explaining setting and changing of a presenting distance of a visual target by a visual target moving mechanism.

FIG. 3 is an explanatory drawing for explaining setting and changing of a presenting distance of the visual target 28 (see FIG. 4) by a visual target moving mechanism 16. The visual target moving mechanism 16 can change the presenting distance of the visual target 28 between 5.0 m (0.2 D) which is a predetermined distance for far vision (hereinafter, referred to as a far vision distance) and 0.4 m (2.5 D) which is a predetermined distance for near vision (hereinafter, referred to as a near vision distance) in a short time by moving the visual target presenting unit 15 in the front-rear direction at a high speed. Note that 0.4 m (2.5 D) is a distance assuming a work with a laptop personal computer, and the setting of the near vision distance is changed according to the type of work (reading book, precision work).

In the full correction value acquiring mode, the visual target moving mechanism 16 adjusts the presenting distance of the visual target 28 (see FIG. 4) to the far vision distance. In the addition power determining mode, the visual target moving mechanism 16 performs and repeats five times, an action of changing the presenting distance of the visual target 28 from the far vision distance to the near vision distance in a short time depending on the change of the power (0 D to 2.0 D) in five stages described above. Note that the definition of the term "short time" will be described later.

Note that in this embodiment, the presenting distance of the visual target 28 (see FIG. 4) is automatically changed by the visual target moving mechanism 16 (visual target moving unit 27). For example, however, the presenting distance may be changed by the manual operation of the examiner.

Figure 4:
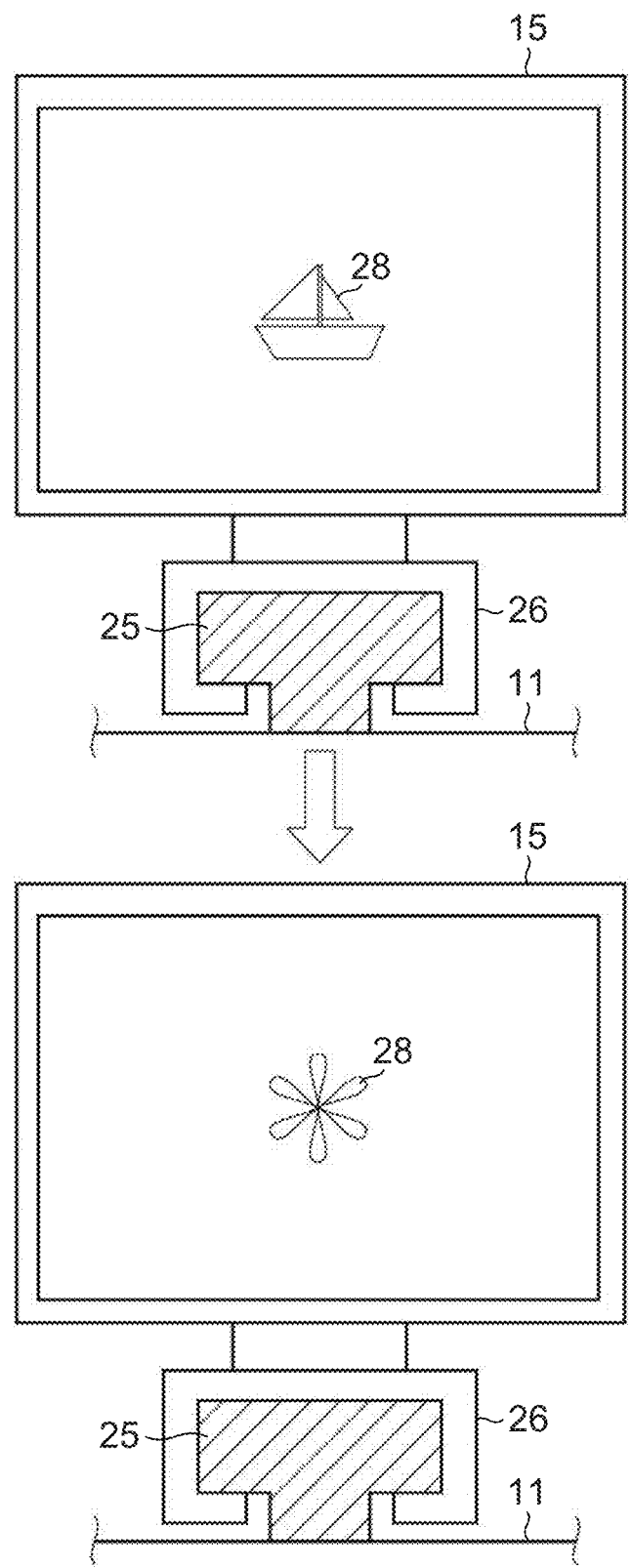
FIG. 4 is an explanatory drawing for explaining examples of the visual target presented by a visual target presenting unit.

FIG. 4 is an explanatory drawing for explaining examples of the visual target 28 presented (displayed) by a visual target presenting unit 15. As illustrated in FIG. 4, the visual target presenting unit 15 changes a display mode of the visual target 28 between a case where the presenting distance of the visual target 28 is the far vision distance (upper part in the drawing) and a case of the near vision distance (lower part in the drawing). For example, the visual target 28 for far vision is desirably a landscape or the like which gives no strange feeling by being far away, and it is preferable that the visual target 28 for near vision is a character, a geometric pattern, or the like. Note that the display mode of the visual target 28 by the visual target presenting unit 15 may be fixed irrespective of the presenting distance.

In this embodiment, a liquid crystal display is used as the visual target presenting unit 15. However, for example, it is possible to use, as the visual target presenting unit 15, various types of devises or members which can present (display) the visual target 28 such as a visual target plate or the like on which an image of the visual target 28 is drawn.

Returning back to FIG. 1, the dichroic mirrors 17R, 17L correspond to optical members of the present invention. The dichroic mirror 17R is supported at a position forward of the wave-front sensor 18R via a supporting member, not illustrated, and is arranged on an optical path OR connecting the visual target 28 and the right eye of the subject's eyes E. In contrast, the dichroic mirror 17L is supported at a position forward of the wave-front sensor 18L via a supporting member, not illustrated, and is arranged on an optical path OL connecting the visual target 28 and the left eye of the subject's eyes E. The dichroic mirrors 17R, 17L are rotationally adjustable about an axis perpendicular to an upper surface of the table 11, respectively.

Each of the dichroic mirrors 17R, 17L transmits a visible light (wavelength range: approximately 380 nm to 780 nm) and reflects lights having wavelength ranges different from visible lights for example, near infrared light (wavelength range: approximately 800 nm to 1100 nm). Accordingly, an image light of the visual target 28 transmits through the dichroic mirrors 17R, 17L, and thus the visual target 28 is visible for both subject's eyes E.

The dichroic mirror 17R reflects a near infrared light LB (which corresponds to a measuring light of the present invention) entering from a wave-front sensor 18R, described later, to the right eye of the subject's eyes E. Accordingly, the near infrared light LB proceeds along the optical path OR and enters the right eye of the subject's eyes E via the addition power adding unit 14R and the eyepiece 13R. Therefore, the near infrared lights LA, LB having two wavelengths, that is, the near infrared light LB and the near infrared light LA emitted from the above described infrared source 12R, enter the right eye of the subject's eyes E. The near infrared lights LA, LB entering the right eye of the subject's eyes E are reflected by the right eye, parts of the reflected lights proceed along the optical path OR and enter the dichroic mirror 17R. The dichroic mirror 17R reflects the near infrared lights LA, LB entering from the right eye of the subject's eyes E toward the wave-front sensor 18R.

The dichroic mirror 17L reflects a near infrared light LB entering from a wave-front sensor 18L, described later, to the left eye of the subject's eyes E. Accordingly, the near infrared light LB proceeds along the optical path OL and enters the left eye of the subject's eyes E via the addition power adding unit 14L and the eyepiece 13L. Therefore, the near infrared lights LA, LB having two wavelengths, that is, the near infrared light LB and the near infrared light LA emitted from the above described infrared source 12L, enter the left eye of the subject's eyes E in the same manner as the right eye. The near infrared lights LA, LB entering the left eye of the subject's eyes E are reflected by the left eye, parts of the reflected lights proceed along the optical path OL and enter the dichroic mirror 17L. The dichroic mirror 17L reflects the near infrared lights LA, LB entering from the left eye of the subject's eyes E toward the wave-front sensor 18L.

The wave-front sensors 18R, 18L correspond to the ocular characteristic acquiring unit of the present invention. The wave-front sensors 18R, 18L are measurement instruments capable of continuously measuring (for example, 30 frames per second (fps)), and can measure optical characteristics (spherical equivalent power, spherical aberration, and other aberrations) of the subject's eyes E. The wave-front sensors 18R, 18L are also capable of measuring eye positions (gaze direction) of both subject's eyes E, measuring convergence angles of both subject's eyes E, and observing the anterior eye parts (detecting pupillary diameters and pupillary centers).

The wave-front sensor 18R is provided at a position shifted from the position of the dichroic mirror 17R in a direction perpendicular to the optical path OR (the right side of the dichroic mirror 17R in the drawing), and faces the dichroic mirror 17R. The wave-front sensor 18L is provided at a position shifted from the position of the dichroic mirror 17L in a direction perpendicular to the optical path OL (the left side of the dichroic mirror 17L in the drawing), and faces the dichroic mirror 17L. Note that the wave-front sensors 18R, 18L are rotationally adjustable about an axis perpendicular to an upper surface of the table 11, respectively.

The wave-front sensor 18R emits a near infrared light LB toward the dichroic mirror 17R, receives the near infrared lights LA, LB having two wavelengths, which are reflected by the dichroic mirror 17R, and outputs light receiving signals for each wavelength range to the device main body 19. Likewise, the wave-front sensor 18L emits a near infrared light LB toward the dichroic mirror 17L, receives the near infrared lights LA, LB having two wavelengths, which are reflected by the dichroic mirror 17L, and outputs light receiving signals for each wavelength range to the device main body 19.

The wave-front sensors 18R, 18L each include an anterior eye part observation system 29A (see FIG. 5) configured to receive a near infrared light LA having a wavelength of 950 nm to acquire images of the anterior eye parts of the subject's eyes E and output a light receiving signal used for measurement (including detection, sensing, examination, and determination) of alignment, eye positions (gaze directions), states of convergence, and pupillary diameters of both eyes. The wave-front sensors 18R, 18L each include an aberration measurement system 29B (see FIG. 5) configured to receive a near infrared light LB having a wavelength of 840 nm and output a light receiving signal used for measurement of optical characteristics (spherical equivalent power, spherical aberration, and other aberrations) of both subject's eyes E.

In this manner, according to the this embodiment, the near infrared lights LA, LB having two wavelengths reflected from the dichroic mirrors 17R, 17L are used as measuring lights for measuring the ocular characteristics (eye position, convergence angle, pupillary diameter, optical characteristics, and the like) of both subject's eyes E. Accordingly, the ocular characteristics of both subject's eyes E can be measured in a state in which both subject's eyes E look at the visual target 28 visually (with natural vision), that is, in a state in which convergence occurs in both eyes and the convergence induces the convergence accommodation.

<Configuration of Wave-Front Sensor>

Figure 5:
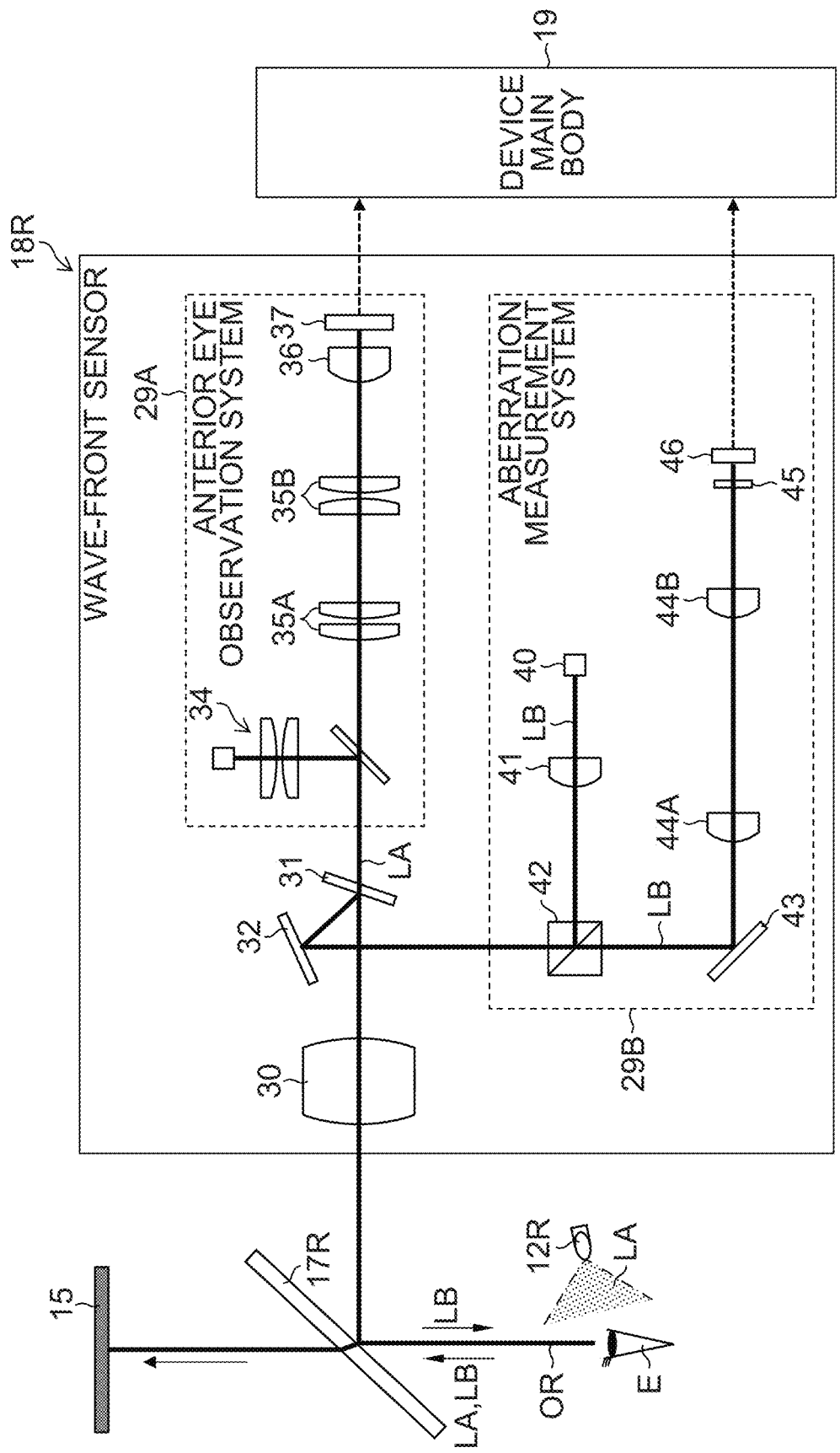
FIG. 5 is a block diagram illustrating a configuration of a wave-front sensor.

FIG. 5 is a block diagram illustrating a configuration of a wave-front sensor 18R. As illustrated in FIG. 5, the wave-front sensor 18R includes an objective lens 30, a dichroic mirror 31, and a mirror 32 in addition to the anterior eye part observation system 29A and the aberration measurement system 29B described above.

The objective lens 30 outputs a near infrared light LB having a wavelength of 840 nm entering from the aberration measurement system 29B, described later, through the mirror 32 and the dichroic mirror 31 toward the dichroic mirror 17R. The objective lens 30 receives the near infrared lights LA, LB reflected from the right eye of the subject's eyes E having two wavelengths through the optical path OR and the dichroic mirror 17R, and the like. The objective lens 30 outputs the near infrared lights LA, LB entering from the dichroic mirror 17R toward the dichroic mirror 31.

The dichroic mirror 31 transmits the near infrared light LA having a wavelength of 950 nm and reflects the near infrared light LB having a wavelength of 840 nm. Accordingly, the dichroic mirror 31 reflects the near infrared light LB having a wavelength of 840 nm and entering from the aberration measurement system 29B through the mirror 32, toward the objective lens 30. Of the near infrared lights LA, LB having two wavelengths entering from the objective lens 30, the dichroic mirror 31 causes the near infrared light LA having a wavelength of 950 nm to enter the anterior eye part observation system 29A, and reflects the near infrared light LB having a wavelength of 840 nm toward the mirror 32.

The mirror 32 reflects the near infrared light LB having a wavelength of 840 nm and entering from one of the aberration measurement system 29B and the dichroic mirror 31, toward the other.

The anterior eye part observation system 29A includes an alignment optical system 34, relay lenses 35A, 35B, an imaging lens 36, and CCD-type (Charge-Coupled Device) or CMOS-type (Complementary Metal Oxide Semiconductor) image sensor 37.

The alignment optical system 34 transmits (projects) an alignment light flux to the anterior eye part of the right eye of the subject's eyes E via the dichroic mirror 31, the objective lens 30, the dichroic mirror 17R, and the like. Accordingly, as a bright point image is generated in an image of the anterior eye part acquired by the image sensor 37, described later, it is possible to perform alignment of the wave-front sensor 18R or the like with respect to the right eye.

The relay lenses 35A, 35B outputs the near infrared light LA having a wavelength of 950 nm and entering from the dichroic mirror 31, toward the imaging lens 36. The imaging lens 36 forms an image of the anterior eye part by the near infrared light LA entering from the relay lens 35B, onto a light receiving surface of the image sensor 37.

The image sensor 37 receives (images) the near infrared light LA imaged by the imaging lens 36 and outputs a light receiving signal indicating the image of the anterior eye part of the right eye of the subject's eyes E to the device main body 19.

The aberration measurement system 29B includes a semiconductor device 40 such as Super Luminescent diode (SLD) or the like, a collimator lens 41, a beam splitter 42, a mirror 43, a lens systems 44A, 44B, a Hartmann plate 45, a CCD-type or CMOS-type image sensor 46.

The semiconductor device 40 outputs the near infrared light LB having a wavelength of 840 nm toward the collimator lens 41. The collimator lens 41 transforms the near infrared light LB entering from the semiconductor device 40 into substantially parallel light, and then, outputs toward the beam splitter 42. Note that the semiconductor device 40 is moved according to the power of the subject's eyes E as needed so that the near infrared light LB converges (focuses) on a back of the subject's eyes E.

The beam splitter 42 is a polarizing beam splitter that, for example, reflects S-polarized light and transmits P-polarized light. The beam splitter 42 reflects the near infrared light LB having a wavelength of 840 nm and entering from the collimator lens 41, toward the mirror 32. The beam splitter 42 transmits the near infrared light LB entering from the mirror 32 through the dichroic mirror 31 or the like as-is, and outputs the near infrared light LB toward the mirror 43.

The mirror 43 reflects the near infrared light LB having a wavelength of 840 nm and entering from the beam splitter 42, toward the lens system 44A. The lens systems 44A, 44B outputs the near infrared light LB entering from the mirror 43 toward the Hartmann plate 45.

The Hartmann plate 45 is provided with a number of minute lenses having the same focal distance on the surface thereof. The Hartmann plate 45 divides the near infrared light LB having a wavelength of 840 nm and entering from the lens system 44B into a plurality of light fluxes corresponding to the respective minute lenses, and causes the respective light fluxes to be imaged on a light receiving surface of the image sensor 46.

The image sensor 46 receives (images) the plurality of light fluxes imaged on the light receiving surface by the Hartmann plate 45, and outputs light receiving signals indicating the plurality of point images corresponding to the respective light fluxes to the device main body 19. The lens system 44B and the Hartmann plate 45 move as needed so that the substantially parallel light enters from the lens system 44B into the Hartmann plate 45. The semiconductor device 40, the lens system 44B, and the Hartmann plate 45 may move in conjunction with each other.

The wave-front sensor 18L has the same configuration as the wave-front sensor 18R, and thus description and illustration of the respective parts of the wave-front sensor 18L will be omitted. The wave-front sensor 18L receives the near infrared light LA having a wavelength of 950 nm and reflected from the left eye of the subject's eyes E by the anterior eye part observation system 29A, and outputs the light receiving signal indicating the image of the anterior eye part of the left eye to the device main body 19. The wave-front sensor 18L receives the near infrared light LB having a wavelength of 840 nm and reflected from the left eye of the subject's eyes E by the aberration measurement system 29B, and outputs the light receiving signal indicating the plurality of point images to the device main body 19.

<Configuration of Device Main Body>

Figure 6:
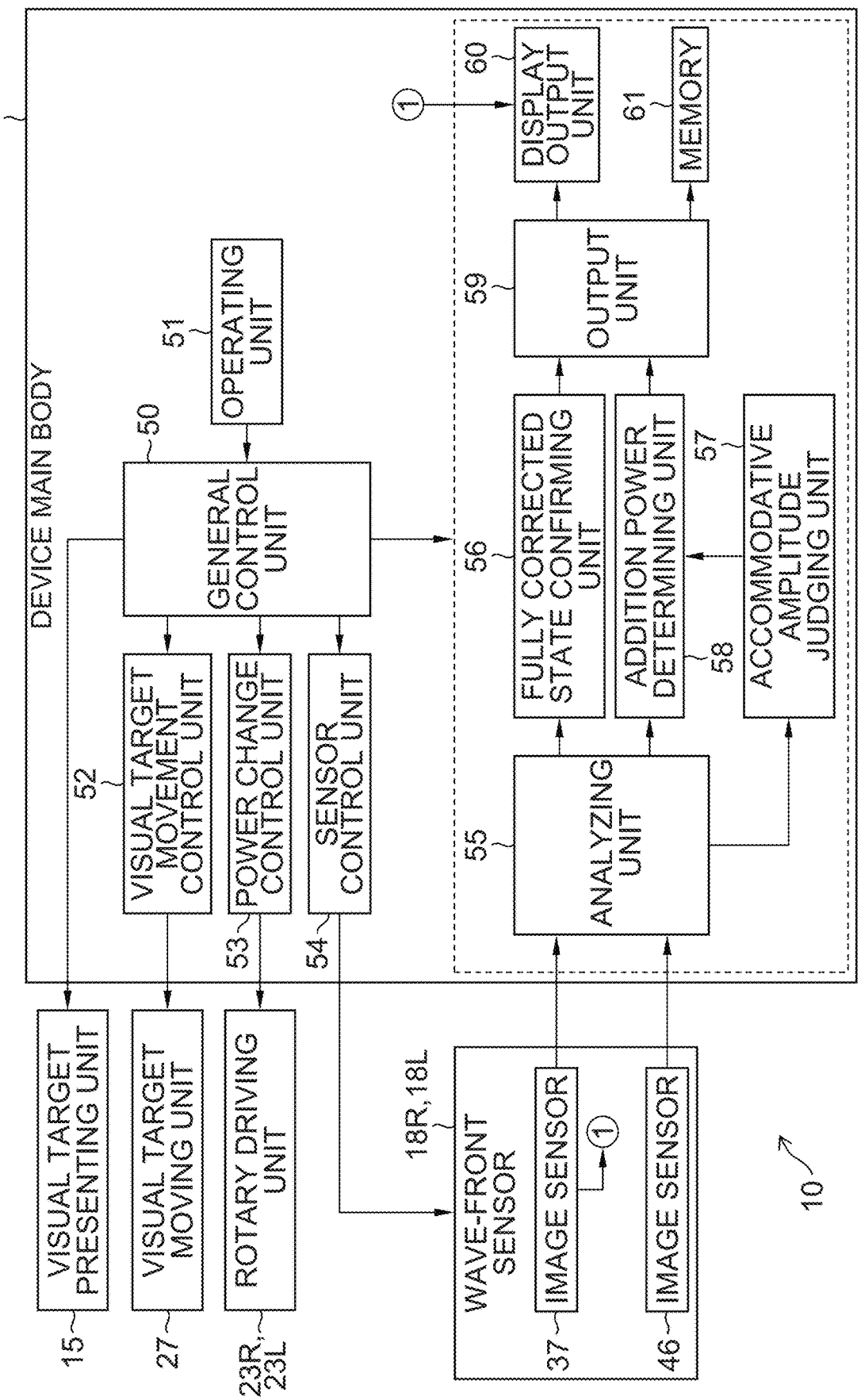
FIG. 6 is a block diagram illustrating a configuration of a device main body.

FIG. 6 is a block diagram illustrating a configuration of a device main body 19. As the device main body 19, for example, various arithmetic processing units such as a personal computer is used.

As illustrated in FIG. 6, the device main body 19 includes a general control unit 50, an operating unit 51, a visual target movement control unit 52, a power change control unit 53, a sensor control unit 54, an analyzing unit 55, a fully corrected state confirming unit 56, an accommodative amplitude judging unit 57, an addition power determining unit 58, an output unit 59, a display output unit 60, and a memory 61. Note that the configuration of the general control unit 50 and the configuration from the visual target movement control unit 52 to the output unit 59 are realized, for example, by making a Central Processing Unit (CPU) or a field-programmable gate array (FPGA) or the like execute a predetermined control program.

The general control unit 50 corresponds to a control unit of the present invention. The general control unit 50 generally controls operations of the respective parts and units of the ophthalmologic device 10 (acquisition of full correction value, determination of addition powers, switching of operation modes of the ophthalmologic device 10) and the like according to the operation instruction which is input to the operating unit 51 by the examiner. A known input device such as a keyboard or a mouse is used as the operating unit 51.

Note that when the operation mode of the ophthalmologic device 10 is the full correction value acquiring mode or the addition power determining mode, the general control unit 50 make the infrared sources 12R, 12L emit the near infrared light LA. Also, the general control unit 50 make the visual target presenting unit 15 display the visual target 28 corresponding to the presenting distance.

The visual target movement control unit 52 drives the above described visual target moving mechanism 16 (visual target moving unit 27) to move the visual target presenting unit 15 in the front-rear direction to set the presenting distance of the visual target 28 under the control of the general control unit 50.

The power change control unit 53 respectively controls the above described addition power adding unit 14R (rotary driving unit 23R) and the addition power adding unit 14L (rotary driving unit 23L) respectively to rotate the turrets 21R, 21L under the control of the general control unit 50 so as to change addition powers to be added to both subject's eyes E.

The sensor control unit 54 respectively drives and makes the above described wave-front sensors 18R, 18L output the near infrared light LB, and drives both of the image sensors 37, 46 (images the near infrared lights LA, LB and outputs light receiving signals) under the control of the general control unit 50.

The analyzing unit 55 constitutes the ocular characteristic acquiring unit of the present invention together with the above described wave-front sensors 18R, 18L. The analyzing unit 55 is configured to analyze light receiving signals output from the image sensors 37, 46 of both the wave-front sensors 18R, 18L and acquire the measurement data of the ocular characteristics of both subject's eyes E. Accordingly, the measurement data of the ocular characteristics of both eyes can be objectively acquired. The measurement data includes the result of acquisition of the optical characteristics of both eyes of the present invention (see FIG. 7).

Figure 7:
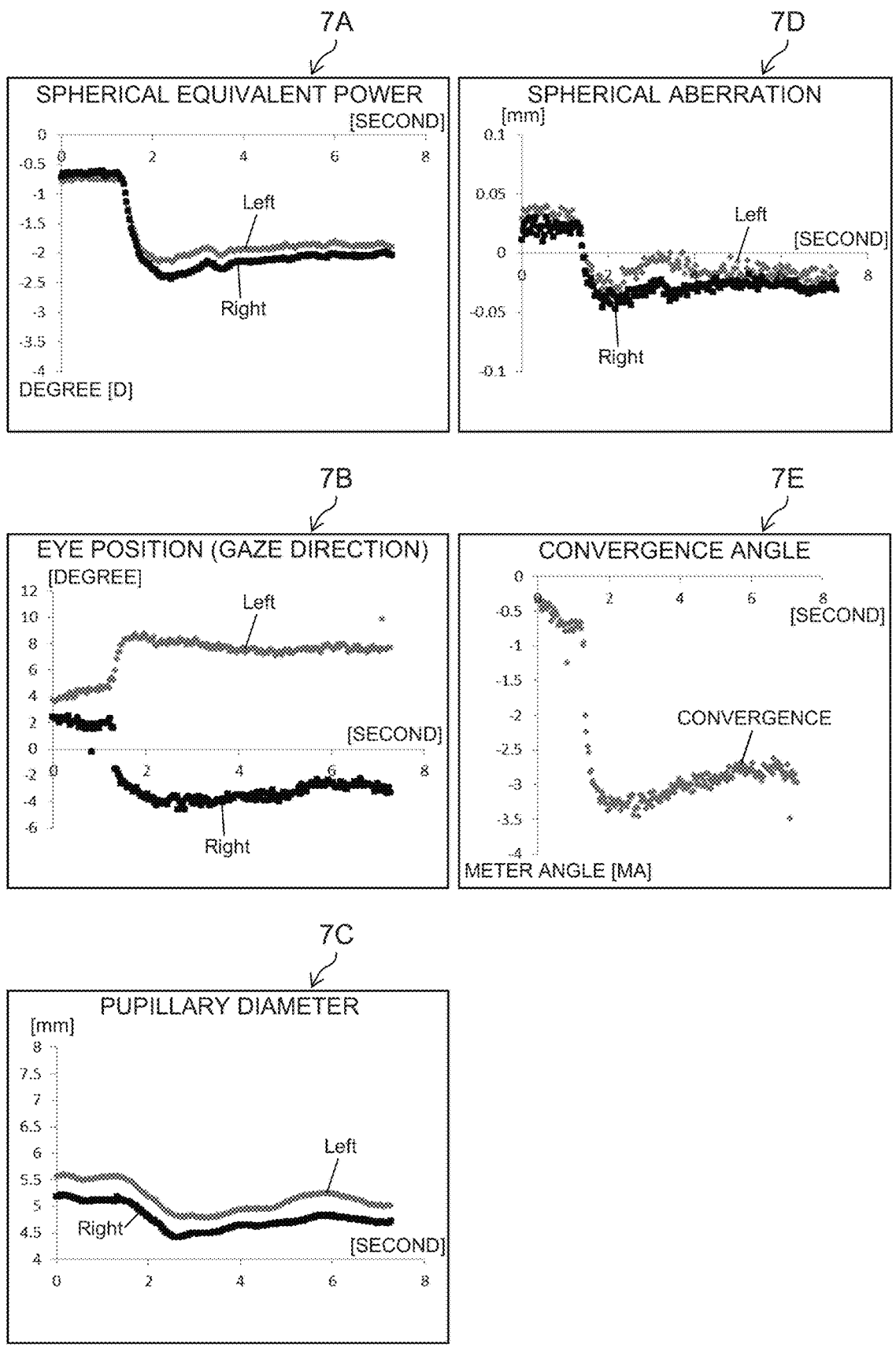
FIG. 7 is graphs showing an example of a measurement data of ocular characteristics of both subject's eyes obtained by measurement by the wave-front sensors.

FIG. 7 is graphs showing an example of a measurement data of ocular characteristics of both subject's eyes E obtained by measurement by the wave-front sensors 18R, 18L. Note that FIG. 7 is a measurement data of the ocular characteristics of both eyes measured by the wave-front sensors 18R, 18L (near vision dynamic measurement, described later) in accordance with the change of the presenting distance of the visual target 28 from the far vision distance to the near vision distance.

As illustrated in FIG. 7, by using the wave-front sensors 18R, 18L, measurement data indicating temporal changes of the spherical equivalent power (see reference numeral 7A), eye position (gaze direction, see reference numeral 7B), the pupillary diameter (see reference numeral 7C), spherical aberration (see reference numeral 7D), the convergence angle (see reference numeral 7E) and the like as the measurement data of the ocular characteristics of both subject's eyes E. Note that the method of analyzing light receiving signals output from the wave-front sensors 18R, 18L and acquiring the respective measurement data of the ocular characteristics described above are known in the related art and thus detailed description will be omitted.

Referring back to FIG. 6, the fully corrected state confirming unit 56 objectively confirms the fully corrected state of both subject's eyes E. Note that the full correction value acquiring mode is performed in a state in which the subject wears a test lens.

When in the full correction value acquiring mode, the fully corrected state confirming unit 56 acquires residual powers of both eyes based on the measurement data of the optical characteristics (spherical equivalent power, astigmatism component) of both subject's eyes E acquired by the analyzing unit 55, and confirms the fully corrected state of both eyes based on the residual powers. Note that the residual powers obtained by the fully corrected state confirming unit 56 is output to the output unit 59. Note that the method of acquiring the residual powers is known in the related art and thus detailed description will be omitted.

In this embodiment, based on the confirmation result by the fully corrected state confirming unit 56, the examiner determines the full correction value of both subject's eyes E. Note that the specific method of determining the full correction value will be described later. When the full correction value determined by the examiner is input to the operating unit 51, the full correction value is input to the output unit 59 via the general control unit 50.

The accommodative amplitude judging unit 57 judges the accommodative amplitudes of both subject's eyes E when in the addition power determining mode, which will be explained in detail below. The accommodative amplitude judging unit 57 outputs the determination result of the accommodative amplitudes of both subject's eyes E to the addition power determining unit 58.

When in the addition power determining mode, the addition power determining unit 58 determines addition powers suitable for both subject's eyes E and outputs the result of determination of the powers to the output unit 59, which will be explained in detail below.

The output unit 59 determines prescription values of spectacle lenses for near vision (not illustrated) based on the full correction value of both subject's eyes E input from the operating unit 51 and the addition powers of both eyes input from the addition power determining unit 58, and respectively outputs the prescription values to the display output unit 60 and the memory 61.

The prescription value may be generated by using the optical characteristics of both eyes acquired by the wave-front sensors 18R, 18L in a state in which the presenting distance of the visual target 28 is set to near vision distance and the addition power is set to 0 D, in addition to the full correction values and the addition powers of both subject's eyes E.

In addition, the prescription values include prism powers to correct this phoria-myopia if it is diagnosed that the subject's eyes E have phoria-myopia in a measurement separate from the ophthalmologic device 10. The prism powers are determined based on a measurement result obtained when the examiner measures the phoria angle and accommodative change (see FIG. 19) of the subject's eyes E with a known method. The prism powers are output to the output unit 59 by the examiner via the operating unit 51.

Note that in the full correction value acquiring mode, the output unit 59 outputs the residual power input from the fully corrected state confirming unit 56 to the display output unit 60.

The display output unit 60 is provided with a monitor such as a liquid crystal display or the like and a printer. The display output unit 60 displays prescription values input from the output unit 59 and observed images of both subject's eyes E based on the light receiving signal input from the image sensor 37, and outputs (prints) the prescription values. Note that the display output unit 60 displays residual powers input from the output unit 59 in the full correction value acquiring mode. The memory 61 stores the prescription values input from the output unit 59 in association with, for example, unique identification information of the subject.

Next, the details of an operation of acquiring the full correction value of both subject's eyes E in the full correction value acquiring mode and the operation of determining the addition powers for both eyes in the addition power determining mode will be described.

<Full Correction Value Acquiring Mode>

The full correction value acquiring mode is initially started in a state where the subject wears no test lens. The general control unit 50 causes infrared sources 12R, 12L to emit near infrared light LA when the full correction value acquiring mode is set.

When the full correction value acquiring mode is set, the visual target movement control unit 52 drives the visual target moving unit 27 under the control of the general control unit 50, to set the presenting distance of the visual target 28 to an above described far vision distance. Further, when the full correction value acquiring mode is set, the visual target presenting unit 15 starts to present the visual target 28 corresponding to far vision distance under the control of the general control unit 50.

When the mode is set to the full correction value acquiring mode, the power change control unit 53 drives the rotary driving units 23R, 23L, respectively under the control of the general control unit 50 to set the addition powers to be added to both subject's eyes E to 0 D, that is, to non-added state.

The sensor control unit 54 causes the wave-front sensors 18R, 18L to emit the near infrared light LB under the control of the general control unit 50 when the mode is set to the full correction value acquiring mode. The sensor control unit 54 causes the image sensors 37 of both the wave-front sensors 18R, 18L to image the near infrared light LB and causes the image sensors 46 of both to image the near infrared light LB respectively, and causes the image sensors 37, 46 of both to output light receiving signals to the device main body 19. Accordingly, the measurement data of the optical characteristics (spherical equivalent power, astigmatism component) of both subject's eyes E is analyzed and acquired by the analyzing unit 55, and the residual powers of both eyes are acquired by the fully corrected state confirming unit 56.

The residual powers acquired by the fully corrected state confirming unit 56 are displayed by the display output unit 60 via the output unit 59. Accordingly, provisional full correction values are determined by the examiner, and test lenses corresponding to the full correction values are worn by the subject.

After the test lenses are worn, the emission of the near infrared light LB by the wave-front sensors 18R, 18L, output of light receiving signals by the wave-front sensors 18R, 18L, analysis by the analyzing unit 55 and acquisition of the residual powers of both subject's eyes E by the fully corrected state confirming unit 56 are repeatedly performed under the control of the general control unit 50. The fully corrected state confirming unit 56 then confirms the fully corrected state of both eyes based on whether or not newly acquired residual powers of both eyes are within a range from approximately 0 D to −0.25 D. When the residual powers are not within a range from approximately 0 D to −0.25 D, the fully corrected state confirming unit 56 outputs alarm information indicating such confirmation result and the newly acquired residual powers to the display output unit 60 via the output unit 59. Accordingly, the alarm information and the residual powers are displayed on the display output unit 60.

The examiner adds the powers corresponding to the new residual powers to the test lenses, and then causes the ophthalmologic device 10 to perform the above-described processes repeatedly. From then onward, the above-described processes are repeatedly performed until the residual powers acquired by the fully corrected state confirming unit 56 fall within the range approximately from 0 D to −0.25 D. When the newly acquired residual powers for both eyes fall within the range approximately from 0 D to −0.25 D, the fully corrected state confirming unit 56 outputs completion information indicating such confirmation result to the display output unit 60 via the output unit 59. Accordingly, the completion information is displayed on the display output unit 60. The examiner determines the full correction values of both subject's eyes E based on the powers of the test lenses at this time point, and the full correction values are input to the output unit 59 via the operating unit 51 or the like. Consequently, the objective full correction values of both eyes in a state in which the visual target 28 is naturally viewed with both subject's eyes E, that is, in a state in which both eyes are subjected to convergence can be determined.

Note that the fully corrected state confirming unit 56 may be configured to perform only up to acquisition and output of the residual powers so that the examiner may perform confirmation of the fully corrected state of both subject's eyes E and determination of the full correction values. In contrast, the examiner may input information on the powers of the test lenses to the fully corrected state confirming unit 56 via the operating unit 51 or the like so that the fully corrected state confirming unit 56 may perform up to determination of the full correction values.

<Addition Power Determining Mode>

When the subject's eyes E have above described phoria-myopia, the addition power determining mode is performed in a state in which the phoria-myopia of the subject's eyes E is corrected in advance by a prism (prism lens) or the like.

When the mode is set to the addition power determining mode, the general control unit 50 causes the infrared sources 12R, 12L to emit the near infrared light LA, and causes the wave-front sensors 18R, 18L to emit the near infrared light LB in the same manner as the full correction value acquiring mode described above.

When the mode is set to the addition power determining mode, the power change control unit 53 drives the rotary driving units 23R, 23L under the control of the general control unit 50 to change the addition powers to be added to both subject's eyes E by the addition power adding units 14R, 14L in the order of 0 D, 0.5 D, 1.0 D, 1.5 D, and 2.0 D.

When the mode is set to the addition power determining mode, the visual target movement control unit 52, the sensor control unit 54, and the analyzing unit 55 perform the near vision dynamic measurement, described later, repeatedly for respective addition powers to be added to both subject's eyes E by the addition power adding units 14R, 14L under the control of the general control unit 50. In other words, the general control unit 50 performs repeating control so as to cause the visual target movement control unit 52, the sensor control unit 54, and the analyzing unit 55 to repeatedly perform the near vision dynamic measurement for respective addition powers to be added to both eyes.

The near vision dynamic measurement means to continuously measure the change of the ocular characteristics (such as optical characteristics) of the subject's eyes E by the wave-front sensors 18R, 18L for a fixed time, before and after the presenting distance of the visual target 28 is changed from the far vision distance to the near vision distance in a short time. Note that the "short time" here means a time shorter than time from the presentation of the convergence stimulation for the subject's eyes E until the subject's eyes E starts the convergence accommodation, which is specifically 0.2 seconds or less.

Figure 8:
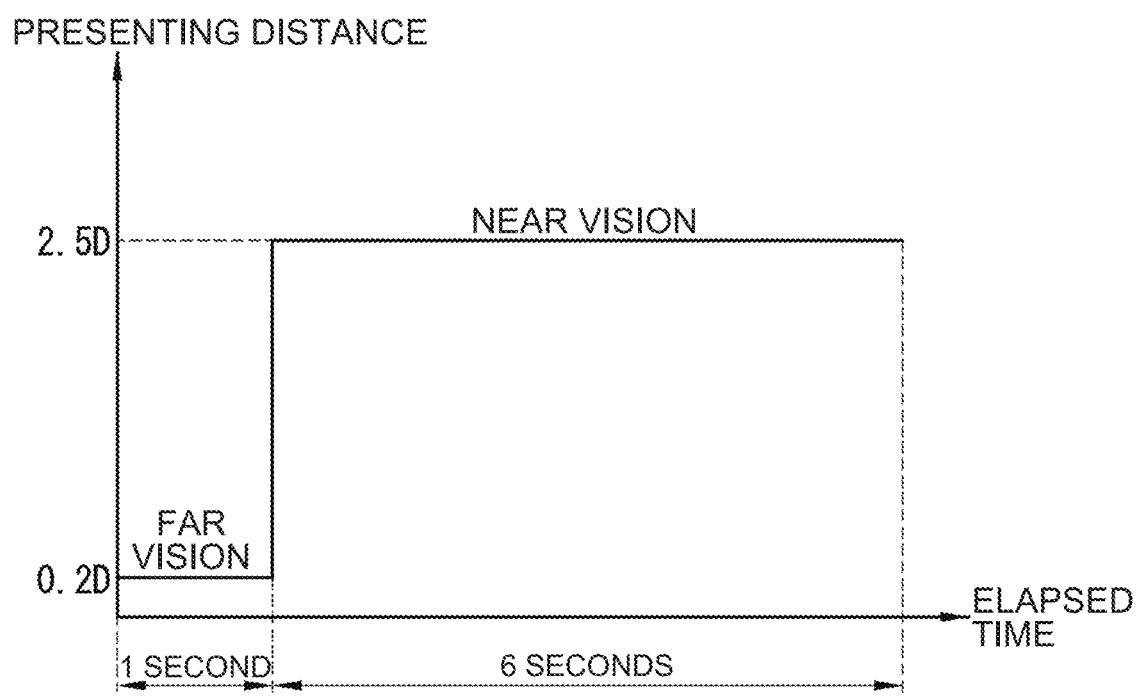
FIG. 8 is an explanatory drawing for explaining an operation of changing the presenting distance of the visual target in the near vision dynamic measurement.

FIG. 8 is an explanatory drawing for explaining an operation of changing the presenting distance of the visual target 28 in the near vision dynamic measurement. As illustrated in FIG. 8, the visual target movement control unit 52 drives the visual target moving unit 27 and keeps a state in which the presenting distance of the visual target 28 is set to the far vision distance for one second, and then changes the presenting distance from the far vision distance to the near vision distance in a short time, and keeps a state in which the presenting distance is set to the near vision distance for six seconds. Note that the respective time may be changed as needed.

The visual target presenting unit 15 presents the visual target 28 corresponding to the far vision distance to both subject's eyes E when the presenting distance of the visual target 28 is the far vision distance and presents the visual target 28 corresponding to the near vision distance to both subject's eyes E when the presenting distance of the visual target 28 is the near vision distance, under the control of the general control unit 50 (see FIG. 4).

The sensor control unit 54 causes the wave-front sensors 18R, 18L to image the near infrared light LA and the near infrared light LB and to output light receiving signals, in association with the change of the presenting distance of the visual target 28. In addition, the analyzing unit 55 analyzes light receiving signals input from the wave-front sensors 18R, 18L and acquires the measurement data of the ocular characteristics, in association with the change of the presenting distance of the visual target 28. Accordingly, it is possible to obtain the measurement data (see FIG. 7 described above) indicating the temporal change of the ocular characteristics of both eyes in the state where any of addition powers described above are added to both subject's eyes E by the addition power adding units 14R, 14L.

Figure 9:
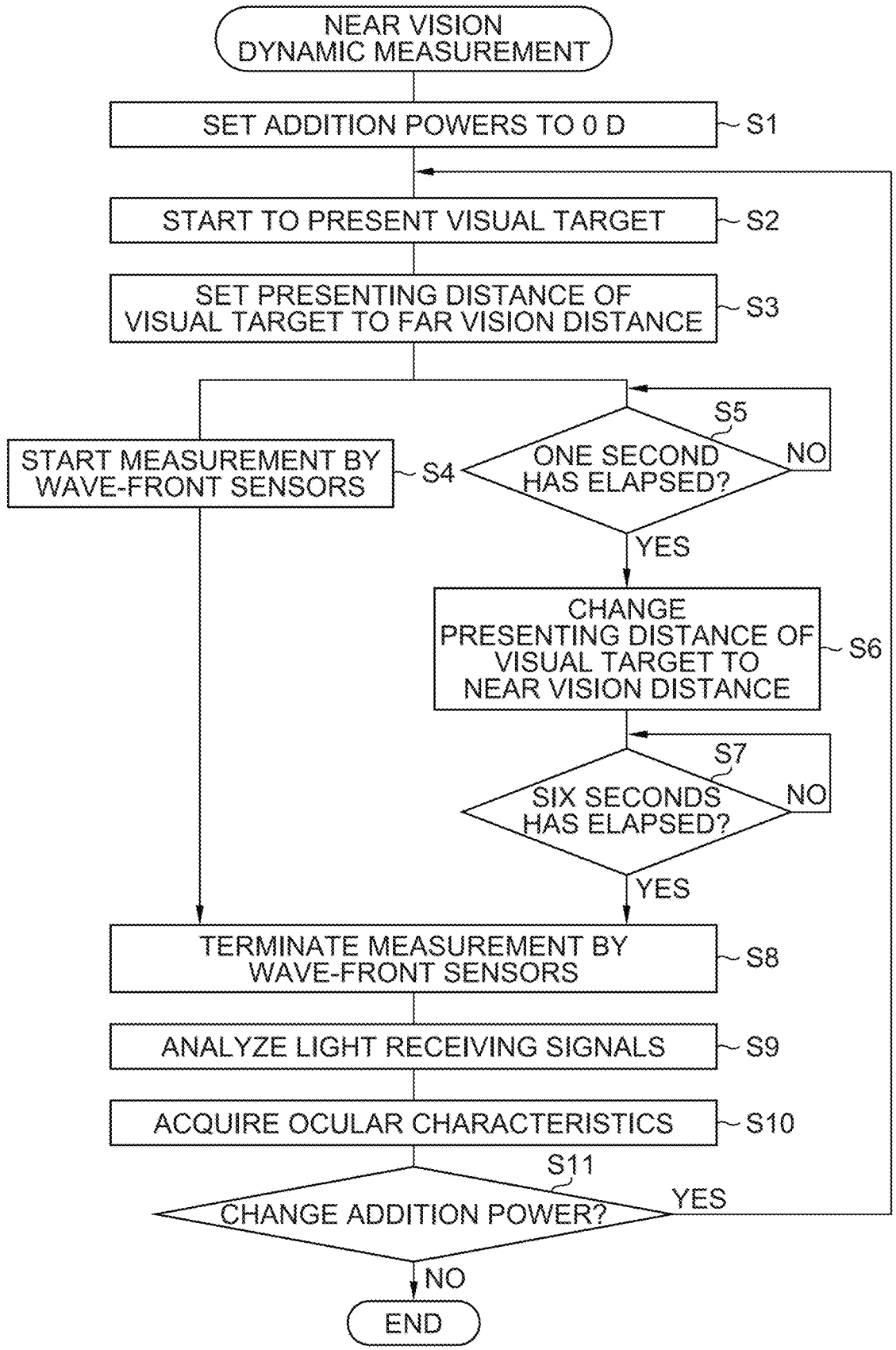
FIG. 9 is a flowchart showing a flow of the near vision dynamic measurement repeatedly performed in an addition power determining mode.

FIG. 9 is a flowchart showing a flow of the near vision dynamic measurement repeatedly performed in the addition power determining mode (which corresponds to the method of operating the ophthalmologic device of the present invention). As illustrated in FIG. 9, the general control unit 50 causes the infrared sources 12R, 12L to emit the near infrared light LA and controls the sensor control unit 54 to cause the wave-front sensors 18R, 18L to emit the near infrared light LB, when an operation mode is changed to the addition power determining mode by the operating unit 51. The general control unit 50 also controls the power change control unit 53 to drive the rotary driving units 23R, 23L, thereby causing the addition power adding units 14R, 14L to set the addition powers to be added to both subject's eyes E to 0 D (Step S1).

When the measurement start operation is performed by the operating unit 51, the general control unit 50 causes the visual target presenting unit 15 to present the visual target 28 corresponding to the far vision distance (Step S2, which corresponds to the visual target presenting step of the present invention). The general control unit 50 controls the visual target movement control unit 52 to drive the visual target moving unit 27 and set the presenting distance of the visual target 28 to the far vision distance (Step S3), and starts measurement of elapse of the time. In addition, the general control unit 50 controls the sensor control unit 54 to cause the wave-front sensors 18R, 18L to start measurement (imaging of the near infrared lights LA, LB and output of light receiving signals) (Step S4, which corresponds to the ocular characteristic acquiring step of the present invention).

When one second has elapsed since the presenting distance of the visual target 28 is set to the far vision distance, the general control unit 50 controls the visual target movement control unit 52 to drive the visual target moving unit 27 so that the presenting distance of the visual target 28 is changed from the far vision distance to the near vision distance (Yes in Step S5 and Step S6, which correspond to a presenting distance changing step of the present invention). In this case, the general control unit 50 causes the visual target presenting unit 15 to present the visual target 28 corresponding to the near vision distance.

The general control unit 50 controls the sensor control unit 54 and maintains (continues) to measure by the wave-front sensors 18R, 18L from one second before to six seconds after the change of the presenting distance of the visual target 28 to the near vision distance (Step S7). The measurement here may be performed such that Hartman images obtained by the image sensor 46 are acquired at a camera rate, for example, at 1/30 second intervals, and are recorded in a memory, and computation of the optical characteristic values may be performed after the measurement is ended. In this case, in this embodiment, since the same visual target 28 is viewed with both subject's eyes E, measurement by the wave-front sensors 18R, 18L is performed in a state in which the visual target 28 is viewed naturally with both subject's eyes E, that is, in a state in which convergence occurs in both eyes. The general control unit 50 ends the measurement by the wave-front sensors 18R, 18L when six seconds have elapsed after the presenting distance has been changed (Step S8).

Subsequently, the general control unit 50 causes the analyzing unit 55 to analyze light receiving signals output from both of the wave-front sensors 18R, 18L (Step S9). Accordingly, it is possible to acquire measurement data indicating the temporal change of the ocular characteristics [optical characteristics (spherical equivalent power), convergence angle] of both eyes in a state in which an addition power of 0 D is added to both subject's eyes E (Step S10). Then, the near vision dynamic measurement for the first time is completed.

After the near vision dynamic measurement for the first time has completed, the general control unit 50 also controls the power change control unit 53 to drive the rotary driving units 23R, 23L, thereby causing the addition power adding units 14R, 14L to change the addition powers to be added to both subject's eyes E to 0.5 D (Yes in Step S13, corresponding to the addition power adding step in the present invention). The general control unit 50 then drives the visual target presenting unit 15, the visual target movement control unit 52, the sensor control unit 54 and the analyzing unit 55 respectively to perform processes from Step S2 to Step S10 described above repeatedly (which corresponds to the repeating control step in the present invention). Accordingly, the near vision dynamic measurement for the second time is performed to acquire measurement data indicating the temporal change of the ocular characteristics of both subject's eyes E in a state in which an addition power of 0.5 D is added to both subject's eyes E.

In the same manner, the near vision dynamic measurement is respectively performed every time when the addition power to be added to both subject's eyes E by the addition power adding units 14R, 14L is changed in the order of 1.0 D, 1.5 D, and 2.0 D (which corresponds to the repeating control step of the present invention). Accordingly, it is possible to acquire measurement data indicating the temporal change of both subject's eyes E in states in which an addition power of 1.0 D, 1.5 D, and 2.0 D are respectively added to both subject's eyes E. Then, the near vision dynamic measurement for each addition power is completed.

<Judgement of Accommodative Amplitude and Determination of Addition Power>

Returning back to FIG. 6, the accommodative amplitude judging unit 57 judges the accommodative amplitudes of both subject's eyes E based on measurement data of optical characteristics, more specifically, measurement data of spherical equivalent power in measurement data of ocular characteristics of both subject's eyes E acquired under the condition of an addition power f 0 D.

The addition power determining unit 58 determines the addition power suitable for both subject's eyes E based on the judgement result by the accommodative amplitude judging unit 57 and measurement data of spherical equivalent power for each addition power. The addition power determining unit 58 determines whether or not both eyes have made accommodation for the visual target 28 after the presenting distance has been changed in the near vision dynamic measurement described above based on the measurement data of convergence angle for each addition power.

The following describes specific examples of the judgment of the accommodative amplitude by the accommodative amplitude judging unit 57 and the determination of the addition power by the addition power determining unit 58.

<First Subject (Late 20's)>

Figure 10:
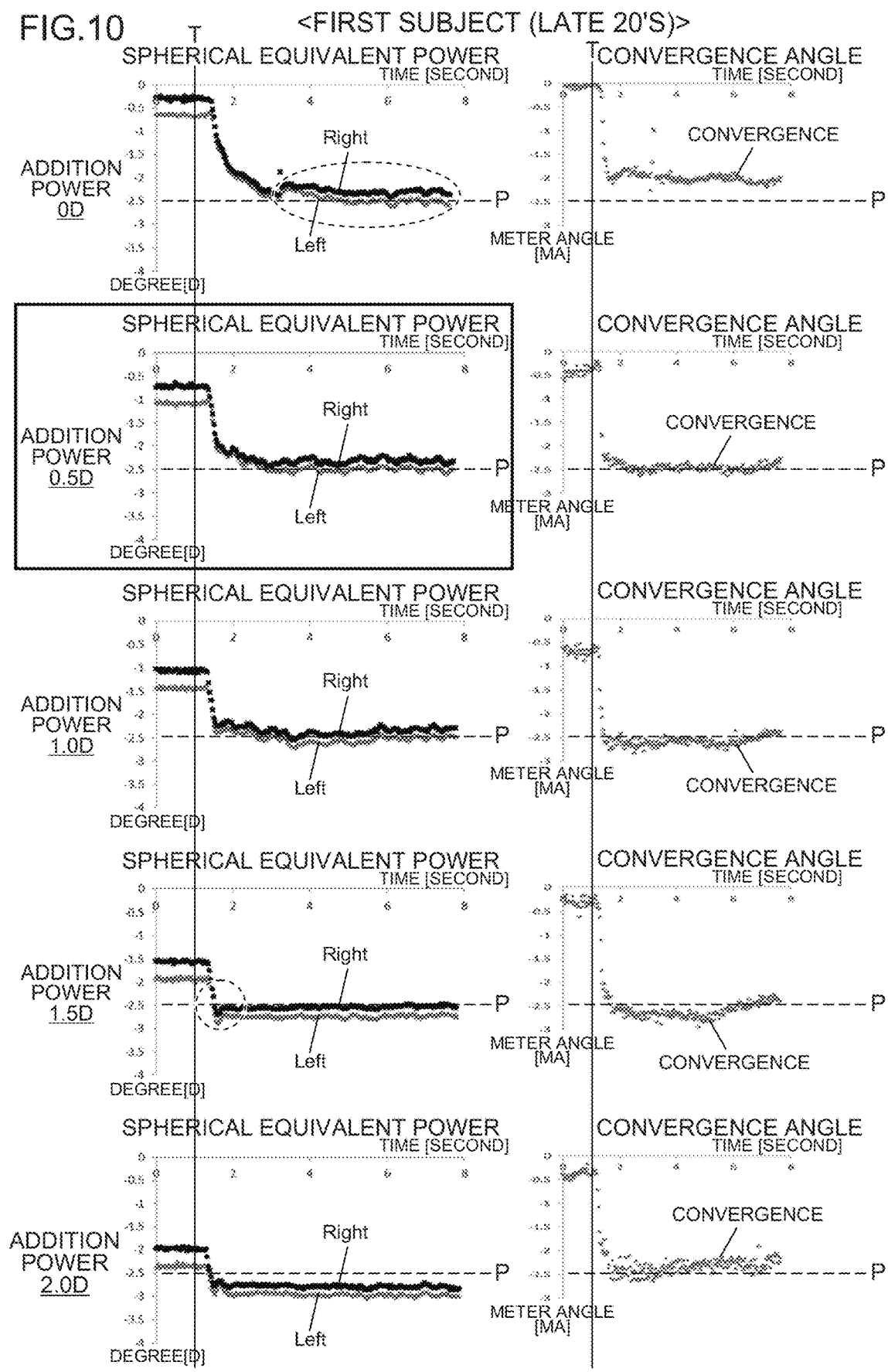
FIG. 10 is an explanatory drawing showing an example of measurement data indicating temporal changes of the spherical equivalent power and the convergence angle for each addition power acquired from subject's eyes of a first subject.

FIG. 10 is an explanatory drawing showing an example of measurement data indicating temporal changes of the spherical equivalent powers and the convergence angle for each addition power acquired from subject's eyes E of a first subject (late 20's). Note that reference sign "T" in the drawing indicates a timing when the presenting distance of the visual target 28 is switched from the far vision distance to the near vision distance. Reference sign "P" in the drawing is a visual target position indicating a position of the visual target 28 at the near vision distance.

(Judgment of Accommodative Amplitude)

As illustrated in FIG. 10, the accommodative amplitude judging unit 57 judges the accommodative amplitudes of both subject's eyes E based on measurement data of the spherical equivalent powers of both eyes acquired under the condition of an addition power of 0 D. For example, when the near vision distance of the visual target 28 is 2.5 D (0.4 m), the accommodative amplitude judging unit 57 judges whether or not the accommodative amplitudes of both eyes satisfy predetermined accommodative amplitude criteria based on whether or not the spherical equivalent powers of both eyes change up to −1.5 D in association with the change of the presenting distance of the visual target 28. The determination criteria (−1.5 D) may be changed as needed according to the setting or the like of the near vision distance of the visual target 28.

Note that the accommodative amplitude judging unit 57 may be configured to judge the accommodative amplitudes of both subject's eyes E according to, for example, the age of the subject, instead of determining the accommodative amplitudes of both subject's eyes E based on the measurement data of the spherical equivalent power acquired under the condition of an addition power of 0 D. In this case, the accommodative amplitude judging unit 57 judges that the accommodative amplitude criteria described above is satisfied when the age of the subject input by the operating unit 51 or the like is equal to or lower than a predetermined certain age, and judges that the accommodative amplitude criteria is not satisfied when the age of the subject is not equal to or lower than the certain age. For example, the subject's eye E that satisfies the accommodative amplitude criteria has no problem for near vision because of the sufficient accommodative amplitude, but spectacle for near vision which reduces fatigue is desirable. In contrast, the subject's eye E which does not satisfy the accommodative amplitude criteria may have a problem for near vision, and thus spectacle for near vision is necessary.

In the case of the first subject, the spherical equivalent powers for both subject's eyes E change to almost −2.5 D in association with the change of the presenting distance of the visual target 28. Therefore, the accommodative amplitude judging unit 57 outputs the determination result indicating that the accommodative amplitudes of both subject's eyes E satisfy the accommodative amplitude criteria, to the addition power determining unit 58.

(Determination of Addition Power)

Based on the determination result of the accommodative amplitude input from the accommodative amplitude judging unit 57, when the accommodative amplitudes of both subject's eyes E satisfy the accommodative amplitude criteria described above, the addition power determining unit 58 determines values and fluctuations of measurement data of the spherical equivalent power for each addition power acquired by the analyzing unit 55.

The spherical equivalent powers of both eyes acquired under the condition of the addition power of 0 D change abruptly to approximately −1.5 D in association with the change of the presenting distance of the visual target 28 in a short time, and then gradually change up to −2.5 D (see reference sign P). The first change up to −1.5 D is assumed to be convergence accommodation. The spherical equivalent powers after the change of the presenting distance are subjected to fluctuations (indicated by a dotted circle).

The spherical equivalent powers of both eyes acquired under the condition of the addition power of 0.5 D change abruptly to approximately −1.5 D in the same manner as the case of 0 D in association with the change of the presenting distance of the visual target 28, and then gradually change up to −2.5 D, and simultaneously, fluctuations in spherical equivalent powers after the change of the presentation are lower than the case of the addition power of 0 D. Also, the spherical equivalent powers of both eyes acquired under the condition of an addition power of 1.0 D change up to −2.5 D in association with the change of the presenting distance of the visual target 28, and fluctuations in spherical equivalent powers after the change of the presenting distance are also lower than the case of the addition power of 0.5 D.

Although the spherical equivalent powers of both eyes acquired under the condition of an addition power of 1.5 D overshoot (indicated by a dotted circle) −2.5 D in association with the change of the presenting distance of the visual target 28, fluctuations in spherical equivalent powers are stabilized after the change of the presenting distance. In this embodiment, by switching the presenting distance of the visual target 28 from the far vision distance to the near vision distance in a short time, it is possible to detect the convergence accommodation of the subject's eyes E and accommodation associated with the change of the presenting distance separately from each other. Consequently, it becomes possible to acquire the state of the convergence accommodation of subject's eyes E that react quickly. Accordingly, it becomes possible to detect the overshooting which cannot be detected when the presenting distance is switched at a low speed so as to easily judge the addition powers which are not suitable for both subject's eyes E. Therefore, it is possible to determine the addition powers suitable for both subject's eyes E.

Further, although the spherical equivalent powers of both eyes acquired under the condition of an addition power of 2.0 D exceed far beyond −2.5 D (over correction is occurring) in association with the change of the presenting distance of the visual target 28, fluctuations in spherical equivalent power is stabilized after presenting distance change.

The addition power determining unit 58 judges the value and fluctuation of the spherical equivalent power for each addition power by analyzing the waveforms of the measurement data of the spherical equivalent power for each addition power with a known method (fitting or the like). The addition power determining unit 58 determines the addition power of 0.5 D at which the spherical equivalent power reaches −2.5 D (including values in the vicinity thereof) and the fluctuations in spherical equivalent powers disappear without being changed only by the convergence accommodation, as the addition powers suitable for both subject's eyes E.

The addition power determining unit 58 may perform Fourier Transformation on the respective measurement data with FFT (Fast Fourier Transformation), for example, and analyze the fluctuation in spherical equivalent power instead of analyzing waveforms of the measurement data of spherical equivalent power for each addition power to determine the addition power at which fluctuations disappear.

<Second Subject (Early 40's)>

Figure 11:
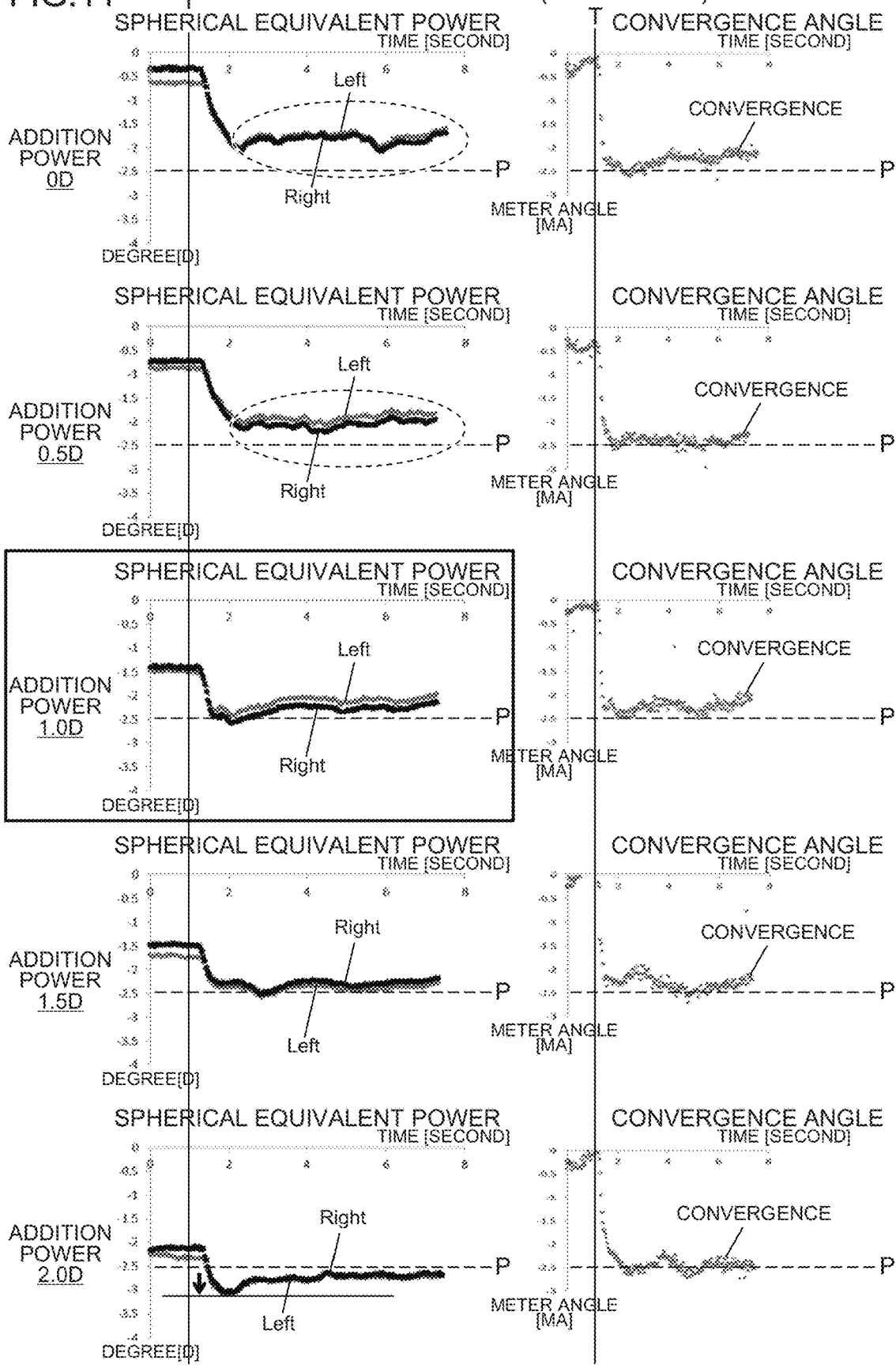
FIG. 11 is an explanatory drawing showing an example of measurement data indicating temporal changes of the spherical equivalent power and the convergence angle for each addition power acquired from subject's eyes of a second subject.

FIG. 11 is an explanatory drawing showing an example of measurement data indicating temporal changes of the spherical equivalent powers and the convergence angle for each addition power acquired from subject's eyes E of a second subject (early 40's).

(Judgment of Accommodative Amplitude)

As illustrated in FIG. 11, in the case of the second subject, measurement data of the spherical equivalent powers of both subject's eyes E acquired under the condition of the addition power of 0 D change to almost −2.0 D in association with the change of the presenting distance of the visual target 28. Therefore, the accommodative amplitude judging unit 57 outputs the judgment result indicating that the accommodative amplitudes of both eyes satisfy the accommodative amplitude criteria, to the addition power determining unit 58.

(Determination of Addition Power)

The addition power determining unit 58 determines the addition power in the same manner as the method described above in FIG. 10, since the accommodative amplitudes of both subject's eyes E satisfy the accommodative amplitude criteria.

The measurement data of the spherical equivalent powers of both eyes acquired respectively under the condition of an addition power of 0 D and an addition power of 0.5 D do not change up to −2.5 D in association with the change of the presenting distance of the visual target 28 and fluctuations (indicated by a dotted circle) occurs even in spherical equivalent powers after the change of the presenting distance.

The measurement data of the spherical equivalent power of both eyes acquired respectively under the conditions of an addition power of 1.0 D and an addition power of 1.5 D changes up to values in the vicinity of −2.5 D in association with the change of the presenting distance of the visual target 28, and fluctuations in spherical equivalent powers after the change of the presentation are lower than the case of the addition power of 0.5 D.

Although the spherical equivalent powers of both eyes acquired under the condition of an addition power of 2.0 D exceed far beyond −2.5 D (over correction) in association with the change of the presenting distance of the visual target 28, fluctuations in spherical equivalent powers are stabilized after the change of the presenting distance.

The addition power determining unit 58 analyzes the waveforms of the measurement data or analyzes fluctuations by Fourier transform, and judges the value and fluctuation of the spherical equivalent power for each addition power. Thereby, the addition power determining unit 58 determines that an addition power 1.0 D at which the spherical equivalent powers reach −2.5 D and fluctuations in spherical equivalent powers disappear, as the addition powers suitable for both subject's eyes E <Third Subject (Late 40's)>

Figure 12:
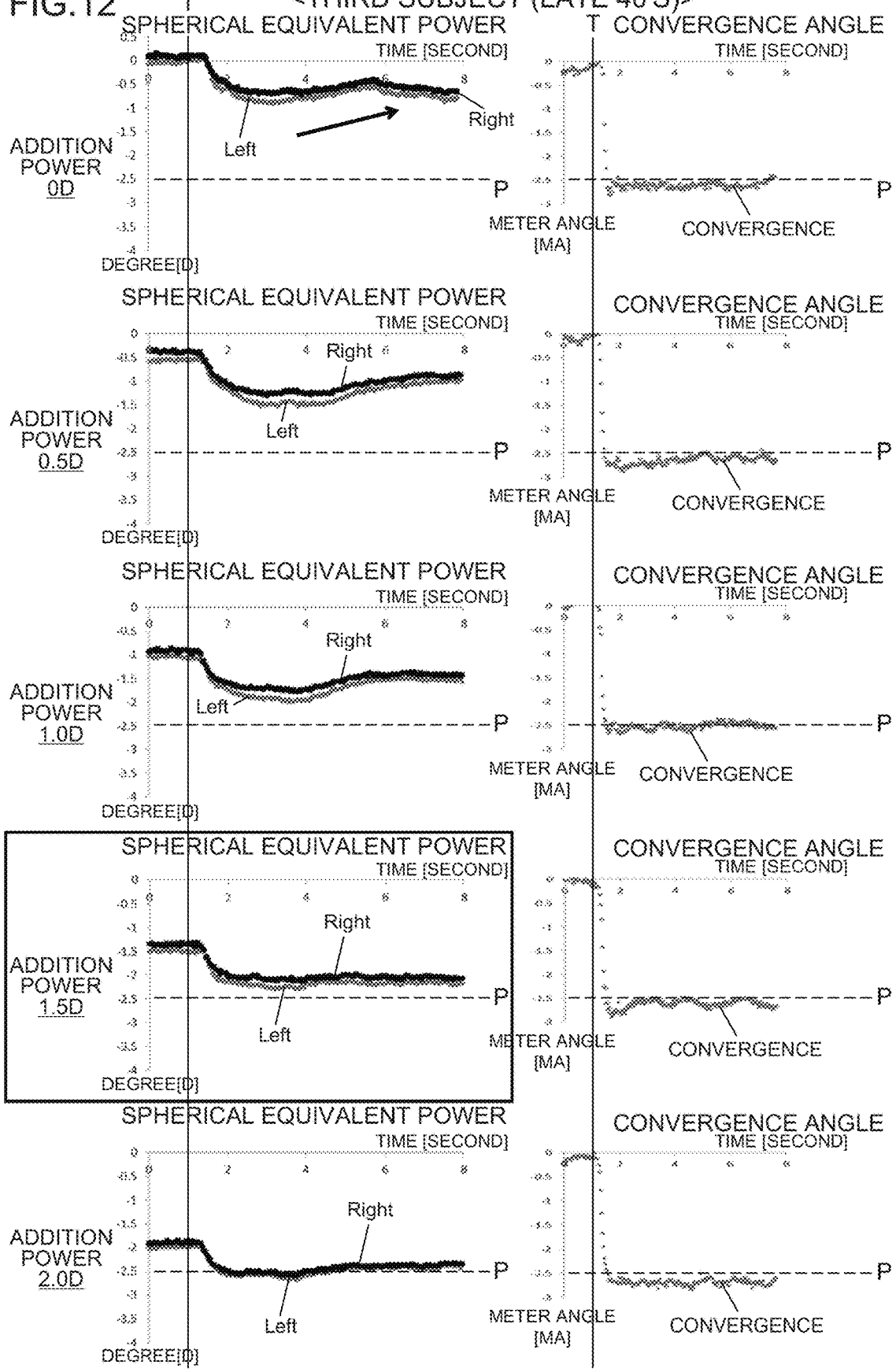
FIG. 12 is an explanatory drawing showing an example of measurement data indicating temporal changes of the spherical equivalent power and the convergence angle for each addition power acquired from subject's eyes of a third subject.

FIG. 12 is an explanatory drawing showing an example of measurement data indicating temporal changes of the spherical equivalent powers and the convergence angle for each addition power acquired from subject's eyes E of a third subject (late 40's).

(Judgment of Accommodative amplitude)

As illustrated in FIG. 12, in the case of the third subject, the measurement data of the spherical equivalent powers of both subject's eyes E acquired under the condition of the addition power of 0 D change only to around −1.0 D in association with the change of the presenting distance of the visual target 28, and the spherical equivalent powers show a "return" which becomes gradually closer to the value before the change of the presenting distance with the elapse of the time (see an arrow in the drawing). In this case, the accommodative amplitude judging unit 57 outputs the judgment result indicating that the above-described accommodative amplitudes of both subject's eyes E do not satisfy the accommodative amplitude criteria but remain a little, to the addition power determining unit 58. Note that, as described above, the judgment of whether or not the accommodative amplitudes of both subject's eyes E do not satisfy the accommodative amplitude criteria but remain a little, may be performed based on the age of the subject.

(Determination of Addition Power)

Based on the judgment result of the accommodative amplitudes input from the accommodative amplitudes judging unit 57, when the accommodative amplitudes of both subject's eyes E do not satisfy the accommodative amplitude criteria, but satisfy a predetermined minimum criteria and the "return" occurs in the measurement data of the spherical equivalent powers, the addition power determining unit 58 determines the addition powers based on the judgment result of the return amount of the spherical equivalent powers for each addition power.

In the measurement data of the spherical equivalent powers of both eyes acquired respectively under the condition of the addition power from 0 D to the addition power 1.0 D, the "return" occurs with the elapse of the time after the change of the presenting distance of the visual target 28.

In contrast, in the measurement data of the spherical equivalent powers of both eyes acquired respectively under the conditions of the addition power of 1.5 D and the addition power of 2.0 D, the return amount of the spherical equivalent powers after the change of the presenting distance of the visual target 28 is significantly reduced as compared to the case of the addition power of 0 D to the addition power of 1.0 D.

The addition power determining unit 58 judges the return amount of the spherical equivalent powers for each addition power by analyzing the waveforms of the measurement data of the spherical equivalent power for each addition power with a known method (fitting or the like) for example. Then, the addition power determining unit 58 determines the addition power (1.5 D in this embodiment) at which the return amount falls within a predetermined criteria, as the addition powers suitable for both subject's eyes E, based on the judgment result of the return amount of the spherical equivalent powers for each addition power.

<Determination Based on Measurement Data of Convergence Angle>

In FIG. 10 to FIG. 12 described above, the addition power determining unit 58 determines whether or not both eyes have made accommodation for the visual target 28 after the change of the presenting distance in the near vision dynamic measurement for each addition power, based on the measurement data of convergence angle of both subject's eyes E for each addition power. Accordingly, it is possible to determine whether or not the state in which both eyes view the visual target 28 naturally is reproduced in near vision dynamic measurement for each addition power. Note that when the addition power determining unit 58 determines to be "negative", it means that there are problems such that the near vision dynamic measurement may not be performed correctly, or the subject's eyes E cannot accommodate for the visual target 28, and thus an alarm display indicating such determination result is displayed on the display output unit 60 or the like.

<Operation of Ophthalmologic Device of First Embodiment>

Figure 13:
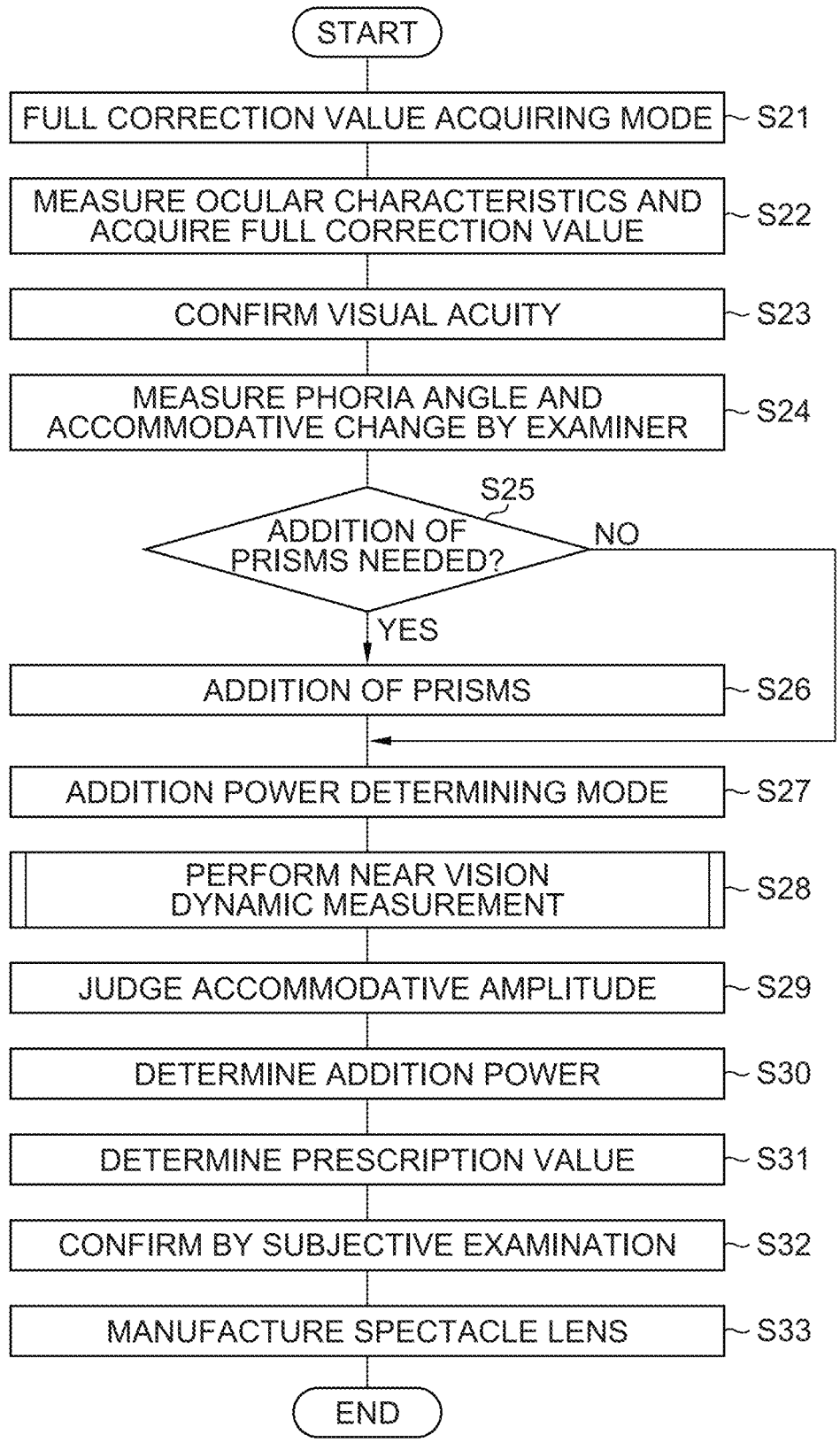
FIG. 13 is a flowchart illustrating a flow of manufacturing a spectacle lens for near vision using the ophthalmologic device, specifically, up to an output of a prescription value by the ophthalmologic device.

FIG. 13 is a flowchart illustrating a flow of a method of manufacturing a spectacle lens for near vision using the ophthalmologic device 10 having the configuration described above (including a method of operating the ophthalmologic device of the present invention), specifically, up to an output of a prescription value by the ophthalmologic device 10.

First, a face of a subject is placed on a face supporting unit of the ophthalmologic device 10, the height of the face is adjusted. Then, when the examiner operates the operating unit 51 and sets the ophthalmologic device 10 to the full correction value acquiring mode (Step S21), the general control unit 50 causes the infrared sources 12R, 12L to start emitting the near infrared lights LA toward the subject's eyes E.

Further, the general control unit 50 controls the sensor control unit 54 to start emitting the near infrared lights LB from the wave-front sensors 18R, 18L. The near infrared lights LB emitted from the wave-front sensors 18R, 18L pass through the dichroic mirrors 17R, 17L or the like and enter respectively into both subject's eyes E. Accordingly, the near infrared lights LA, LB reflected by the right eye of the subject's eyes E pass through the dichroic mirror 17R and enter the wave-front sensor 18R or the like, while the near infrared lights LA, LB reflected by the left eye of the subject's eyes E pass through the dichroic mirror 17L or the like and enters the wave-front sensor 18L.

In addition, under the control of the general control unit 50, the visual target movement control unit 52 sets the presenting distance of the visual target 28 to the far vision distance, the visual target presenting unit 15 presents the visual target 28 corresponding to the far vision distance, and the power change control unit 53 adds an addition power 0 D.

Then, under the control of the general control unit 50, measurement of ocular characteristics of both subject's eyes E is started, imaging of the near infrared light LB and output of light receiving signals are performed by the image sensors 37 of both of the wave-front sensors 18R, 18L, and imaging of the near infrared light LB and output of light receiving signals are performed by the image sensors 46 of both of the wave-front sensors 18R, 18L, and analysis of light receiving signals is performed by the analyzing unit 55. Subsequently, the residual powers of both subject's eyes E in a state in which the subject does not wear the test lenses is acquired by the fully corrected state confirming unit 56, and information relating to the residual powers is output to the display output unit 60 via the output unit 59. The display output unit 60 displays the residual powers.

After determining provisional full correction values based on the residual powers displayed on the display output unit 60, the examiner makes the subject wear test lenses corresponding to the full correction values. The examiner then causes the ophthalmologic device 10 to perform a process of acquiring the above-described residual powers repeatedly in a state in which the subject wears the test lenses.

The fully corrected state confirming unit 56 objectively confirms the fully corrected states of both subject's eyes E based on the determination whether or not the residual powers acquired after the test lenses are worn fall within a range from approximately 0 D to −0.25 D (which corresponds to fully corrected state confirming step of the present invention). When the acquired residual powers are not within a range from approximately 0 D to −0.25 D, the fully corrected state confirming unit 56 outputs alarm information indicating such determination result and the residual powers to the display output unit 60 via the output unit 59. Accordingly, the alarm information and the residual powers are displayed on the display output unit 60.

In this case, the examiner adds powers corresponding to the newly acquired residual powers to the test lenses, and causes the ophthalmologic device 10 to repeatedly perform the residual power acquiring process and confirmation of the fully corrected state or the like as described above. From then onward, each of the above-described processes are repeatedly performed until the residual powers of both subject's eyes E fall within the range approximately from 0 D to −0.25 D.

When it is determined that the newly acquired residual powers for both subject's eyes E fall within the range approximately from 0 D to −0.25 D, the fully corrected state confirming unit 56 outputs completion information indicating such determination result to the display output unit 60 via the output unit 59. Accordingly, the completion information is displayed on the display output unit 60. The examiner determines the full correction values of both subject's eyes E based on the powers of the test lenses worn by the subject, and the full correction values are input to the output unit 59 via the operating unit 51 or the like. Accordingly, objective full correction values of both subject's eyes E are acquired (determined) (Step S22).

Note that it is preferable that antireflection measure for the near infrared light for measurement (wavelength range: from approximately 800 nm to 1100 nm) is applied to the test lenses as described above. The test lenses may be integrated into the addition power adding units 14R, 14L of the ophthalmologic device 10. In this case, the addition powers are added to the full correction values to determine powers, and the lenses corresponding to the determined powers are arranged in the addition power adding units 14R, 14L in order to perform measurement in a state in which the addition powers are added to the full correction values.

The output unit 59 outputs the full correction values input from the fully corrected state confirming unit 56 to the display output unit 60. Accordingly, the full correction values for both eyes are displayed or output on the display output unit 60.

The examiner makes the subject wear the test lenses corresponding to the full correction values, confirms the visual acuity of the subject through the measurement of visual acuity at a distance of 5 m, and then confirms that the visual acuity of the subject's eyes E fall within a range approximately from 1.2 to 1.5, or the maximum visual acuity is achieved for the subject's eyes E (Step S23). The full correction value acquiring mode is completed with the procedure described thus far.

After the completion of the full correction value acquiring mode, the examiner conducts measurement of the phoria angle of subject's eyes E and measurement of accommodative change, as needed, with a known method (see FIG. 19 described later), and the examiner diagnoses whether or not the subject's eyes E have phoria-myopia (Step S24). When the subject's eyes E have phoria-myopia, that is, when addition of a prism is required for the subject's eyes E, the prism is added to the subject's eyes E (Yes in Step S25, Step S26). Note that information on the prism powers is input to the output unit 59 by the examiner via the operating unit 51.

When the examiner operates the operating unit 51 to set the ophthalmologic device 10 to the addition power determining mode (Step S27), the near vision dynamic measurement for each addition power and analysis of the light receiving signal, which have been described in FIG. 9 above, are performed by the wave-front sensors 18R, 18L and the analyzing unit 55 (Step S28). The near vision dynamic measurement by the ophthalmologic device 10 is performed in a state in which the visual target 28 is viewed naturally with both subject's eyes E, that is, in a state in which the convergence occurs in both eyes and the convergence accommodation is induced by this convergence.

Subsequently, judgment of the accommodative amplitudes is performed by the accommodative amplitude judging unit 57, which has been described in FIG. 10 to FIG. 12 above, and determination of the addition power is performed by the addition power determining unit 58 (Step S29, S30, which correspond to the addition power determining step of the present invention). Accordingly, addition powers suitable for both subject's eyes E are determined. The addition power determining unit 58 outputs the determined addition powers to the output unit 59. Then, the addition power determining mode is completed.

When the addition power determining mode is completed, the output unit 59 determines the prescription values for the spectacle lenses (not illustrated) for near vision based on full correction values of both subject's eyes E, addition powers, prism powers (when addition of prisms is required) input respectively from the operating unit 51 and the addition power determining unit 58 (Step S31). The output unit 59 then outputs the determined prescription values respectively to the display output unit 60 and the memory 61. Accordingly, display and output of the prescription values are performed by the display output unit 60 and storage of the prescription values is performed by the memory 61.

The examiner makes the subject wear the test lenses corresponding to the prescription values and performs subjective examination on the subject to fix the prescription values if there is no problems, and prescribes the subject (Step S32). Then, the spectacle lenses (not illustrated) for near vision are manufactured by a manufacture according to the prescription values (Step S33).

<Advantageous Effect of Ophthalmologic Device of First Embodiment>

As described thus far, according to the ophthalmologic device 10 of this embodiment, the near vision dynamic measurement for each addition power is performed in a state in which the visual target 28 is viewed naturally with both subject's eyes E, that is, in a state in which the convergence occurs in both eyes and the convergence accommodation is induced by this convergence. Accordingly, it is possible to present the visual target 28 at a near vision distance with the convergence of both subject's eyes E considered, and measure the ocular characteristics such as the optical characteristics of both eyes with accommodative change induced by the convergence included. Consequently, it is possible to obtain measurement result of the ocular characteristics of both subject's eyes E which is usable for determining optimal addition power closer to natural vision state. Therefore, by using the ophthalmologic device 10, it is possible to determine optimal addition powers closer to the natural vision state.

<Ophthalmologic Device of Second Embodiment>

In the addition power determining mode of the first embodiment described above, repeating control in which the near vision dynamic measurement is repeatedly performed for each individual addition power [0 D, 0.5 D, 1.0 D, 1.5 D, 2.0 D] irrespective of the accommodative amplitudes of the subject's eyes E of the subject.

In this case, in the case of the first subject and the second subject whose subject's eyes E have accommodative amplitudes satisfying the accommodative amplitude criteria as indicated in FIG. 10 and FIG. 11 above, the addition powers suitable for the subject's eyes E are low (For example, 1.0 D or lower). In contrast, in the case of the third subject whose subject's eyes E have accommodative amplitudes unsatisfying the accommodative amplitude criteria as indicated in FIG. 12 above, the addition powers suitable for the subject's eyes E are high (For example, 1.5 D or higher). Therefore, for the first subject and the second subject, there is low requirement to perform the near vision dynamic measurement at the addition power of 1.5 D and the addition power of 2.0 D. In contrast, for the third subject, there is low requirement to perform the near vision dynamic measurement at the addition power of 0.5 D and the addition power of 1.0 D.

Therefore, when the addition power determining mode is set, the ophthalmologic device 10 of the second embodiment determines addition powers to be changed in the addition power determining mode according to the accommodative amplitudes of the subject's eyes E of the subject, and performs the near vision dynamic measurement for each determined addition power. Note that since the ophthalmologic device 10 of the second embodiment has basically the same configuration as the ophthalmologic device 10 of the first embodiment described above, those having the same function and configuration as the first embodiment are designated by the same reference numerals and descriptions thereof are omitted.

Figure 14:
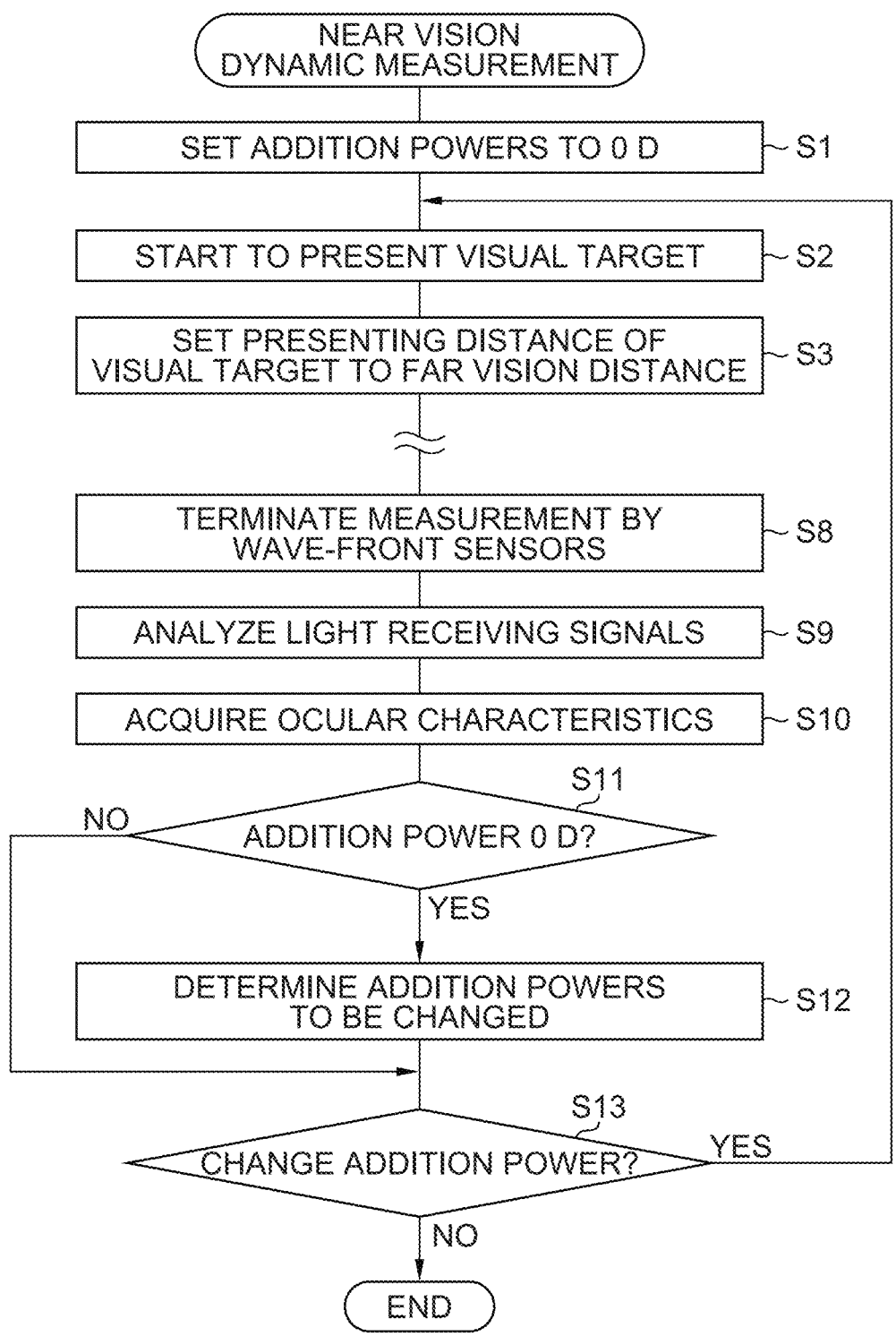
FIG. 14 is a flowchart illustrating a flow of near vision dynamic measurement performed in the addition power determining mode according to a second embodiment.

FIG. 14 is a flowchart illustrating a flow of near vision dynamic measurement performed in the addition power determining mode according to a second embodiment. Note that Step S1 to Step S10 are basically the same as those in the first embodiment described above, and thus detailed description will be omitted.

In Step S10, when measurement data indicating the temporal change of the ocular characteristics [optical characteristics, (spherical equivalent power), convergence angle] of both eyes is acquired in a state in which an addition power of 0 D is added, that is, no addition power is added to both subject's eyes E (Yes in Step S11), the power change control unit 53 judges the accommodative amplitudes of both subject's eyes E. For example, the power change control unit 53 judges the accommodative amplitudes of subject's eyes E in the same determination method as the accommodative amplitude judging unit 57 described above or acquires the judgment result of the accommodative amplitudes from the accommodative amplitude judging unit 57.

Subsequently, the power change control unit 53 determines addition powers to be changed in the addition power determining mode according to the accommodative amplitudes of both subject's eyes E (Step S12). For example, when the accommodative amplitudes of both subject's eyes E satisfy the accommodative amplitude criteria described above, the addition powers to be changed in the addition power determining mode are determined to 0.5 D and 1.0 D, while when the accommodative amplitudes of both subject's eyes E do not satisfy the accommodative amplitude criteria described above, the addition powers to be changed in the addition power determining mode are determined to 1.5 D and 2.0 D by the power change control unit 53. Note that the method of determining the addition powers to be changed is not specifically limited.

After the completion of the first near vision dynamic measurement, the power change control unit 53 drives the rotary driving units 23R, 23L under the control of the general control unit 50 to add the lowest addition power of the previously determined addition powers to both subject's eyes E. The general control unit 50 then drives the visual target presenting unit 15, the visual target movement control unit 52, the sensor control unit 54 and the analyzing unit 55 respectively to perform processes from Step S2 to Step S10 described above, respectively. Accordingly, the second near vision dynamic measurement is performed to acquire measurement data of ocular characteristics of both subject's eyes E. In the same manner, from then onward, the near vision dynamic measurement is performed for each addition power determined by the power change control unit 53 to acquire measurement data for each addition power. Then, in the same manner as the first embodiment, addition powers suitable for both subject's eyes E are determined.

As described above, in the ophthalmologic device 10 of the second embodiment, the addition powers to be changed in the addition power determining mode are determined according to the accommodative amplitudes of both subject's eyes E so that near vision dynamic measurement can be selectively performed at addition powers corresponding to the accommodative amplitudes of the subject's eyes E. Accordingly, it is possible to shorten time required for determining the addition powers suitable for both subject's eyes E.

<Ophthalmologic Device of Third Embodiment>

Next, the ophthalmologic device 10 of the third embodiment will be described. In the respective embodiments described above, the prism powers for correcting the phoria-myopia are determined separately from the ophthalmologic device 10. However, the ophthalmologic device 10 according to the third embodiment automatically determines the prism powers as well.

Figure 15:
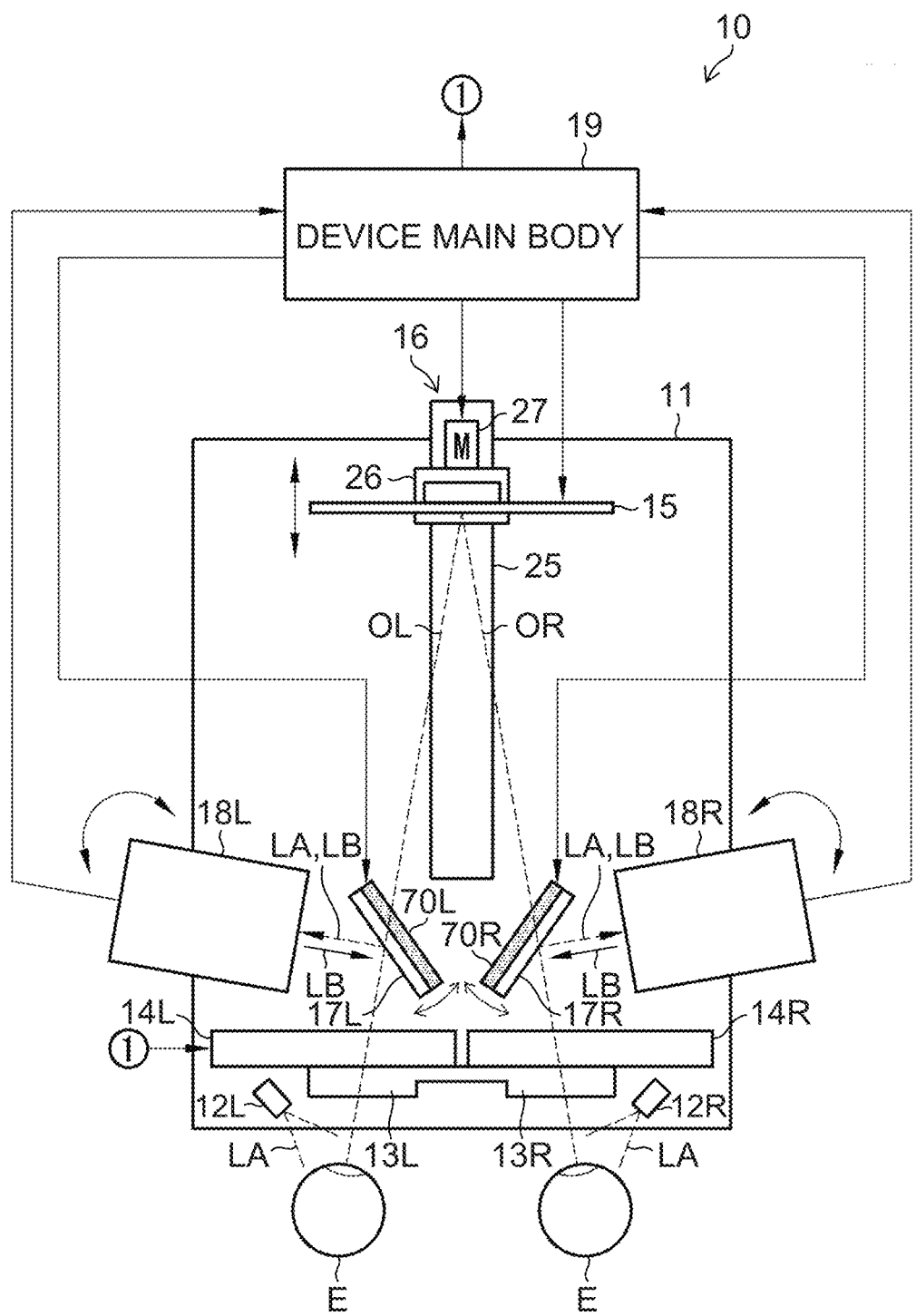
FIG. 15 is a schematic top view of an ophthalmologic device according to a third embodiment.
Figure 16:
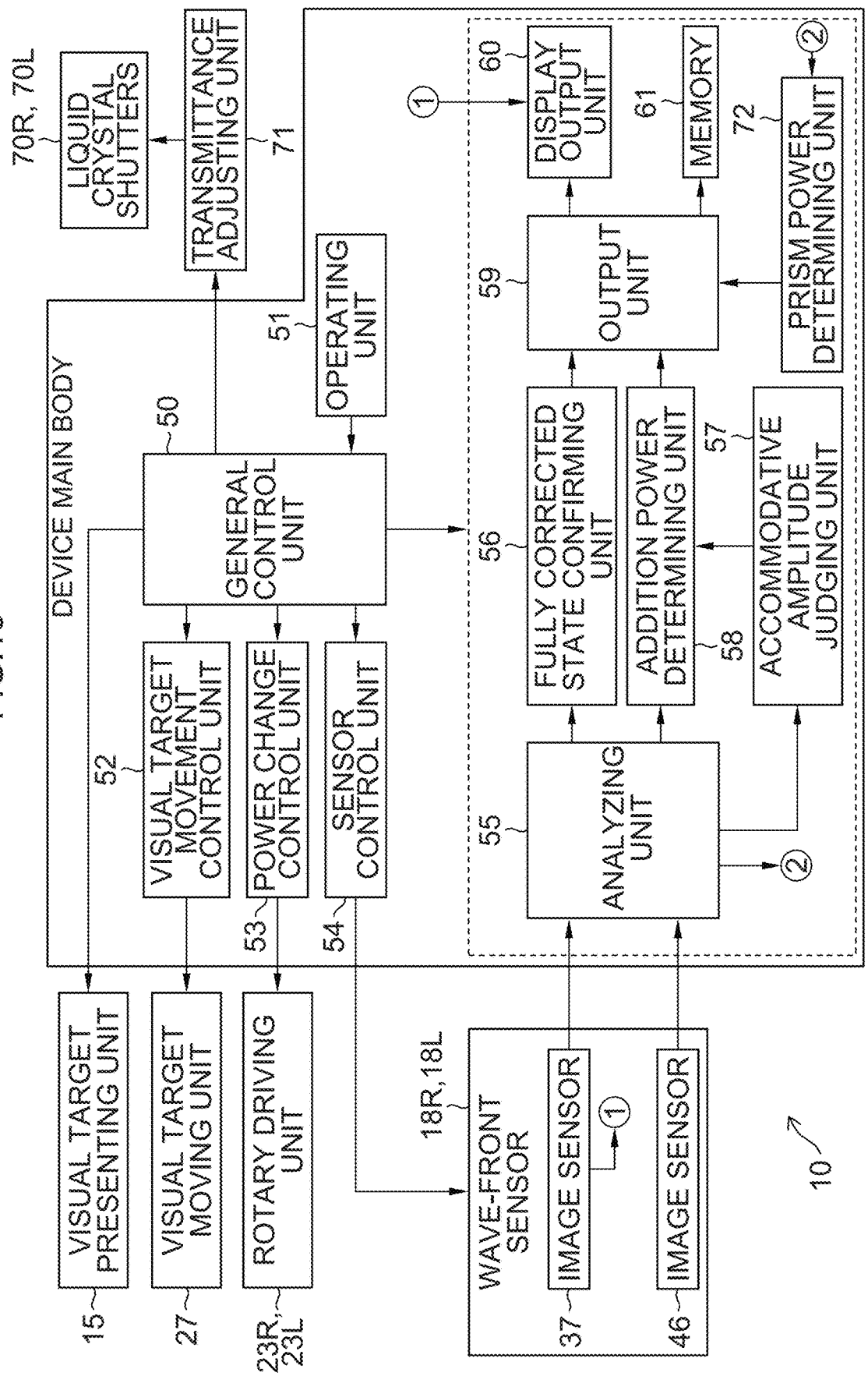
FIG. 16 is a block diagram illustrating a configuration of a device main body of the ophthalmologic device according to the third embodiment.

FIG. 15 is a schematic top view of an ophthalmologic device 10 according to the third embodiment. FIG. 16 is a block diagram illustrating a configuration of a device main body 19 of the ophthalmologic device 10 according to the third embodiment. As illustrated in FIG. 15 and FIG. 16, the ophthalmologic device 10 of the third embodiment has a configuration basically the same as the ophthalmologic device 10 of the first embodiment, except some differences. The differences exist in that: the ophthalmologic device 10 according to the third embodiment includes liquid crystal shutters 70R, 70L provided on the table 11, a transmittance adjusting unit 71 and a prism power determining unit 72 provided on the device main body 19; and the ophthalmologic device 10 according to the third embodiment has a prism power determination mode as an additional operation mode. Therefore, those having the same function or configuration as the first embodiment are designated by the same reference signs and description thereof will be omitted.

The liquid crystal shutter 70R is mounted on a surface of the dichroic mirror 17R on the visual target presenting unit 15 side, and the liquid crystal shutter 70L is mounted on the surface of the dichroic mirror 17L on the visual target presenting unit 15 side. Accordingly, the liquid crystal shutters 70R, 70L are disposed on optical paths OR, OL respectively. Therefore, the right subject's eye E views the visual target 28 through the dichroic mirror 17R and the liquid crystal shutter 70R, and the left eye of the subject's eyes E views the visual target 28 via the dichroic mirror 17L and the liquid crystal shutter 70L.

The liquid crystal shutters 70R, 70L respectively include transmitting regions through which visible lights (image light of the visual target 28) proceeding along the optical paths OR, OL pass. The liquid crystal shutters 70R, 70L can arbitrarily adjust the transmittance of lights transmitted respectively through the transmitting regions by arbitrarily changing the densities of the transmitting regions. Accordingly, brightness of the visual target 28 viewed with both subject's eyes E can be adjusted individually. The transmittances of the liquid crystal shutters 70R, 70L are adjusted by the device main body 19.

Note that positions and configurations of the liquid crystal shutters 70R, 70L are not specifically limited as long as the brightness of the visual target 28 viewed with both subject's eyes E can be individually adjusted. However, in view of preventing the near infrared lights LA, LB reflected by both subject's eyes E from being attenuated by the liquid crystal shutters 70R, 70L, it is preferable that the liquid crystal shutters 70R, 70L are disposed between the dichroic mirrors 17R, 17L and the visual target presenting unit 15.

When the prism power determination mode is set, the visual target movement control unit 52 drives the visual target moving unit 27 under the control of the general control unit 50 to set the presenting distance of the visual target 28 to the near vision distance described above. Also, when the prism power determination mode is set, the visual target presenting unit 15 starts to present the visual target 28 corresponding to the near vision distance under the control of the general control unit 50.

Figure 17:
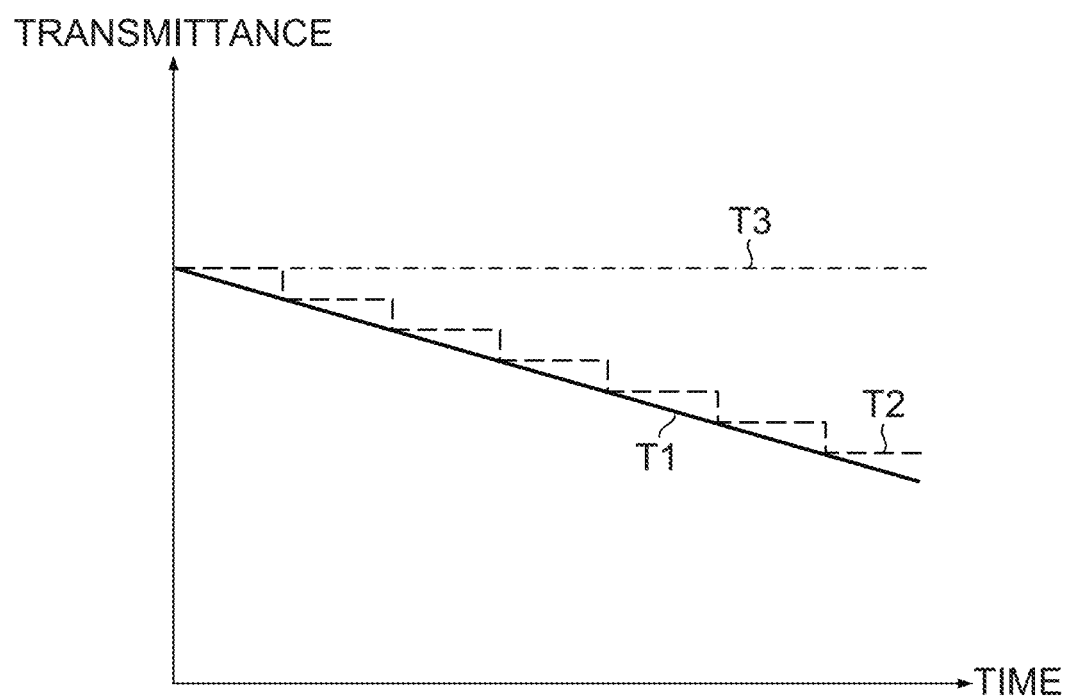
FIG. 17 is an explanatory drawing for explaining an adjustment of transmittance of a liquid crystal shutter by a transmittance adjusting unit.

FIG. 17 is an explanatory drawing for explaining adjustment of transmittances of liquid crystal shutters 70R, 70L by the transmittance adjusting unit 71. As illustrated in FIG. 17, when the prism power determination mode is set, the transmittance adjusting unit 71 adjusts the transmittances (densities) of the respective transmitting regions of the liquid crystal shutters 70R, 70L under the control of the general control unit 50.

Specifically, the transmittance adjusting unit 71 reduces the transmittance of one of the liquid crystal shutters 70R, 70L, which corresponds to a non-dominant eye of subject's eyes E continuously (see reference sign T1) or step by step (see reference sign T2), with elapse of the time. For example, in this embodiment, the transmittance is decreased by 5% every second. Then, after 10 seconds has elapsed in a state in which one of the liquid crystal shutters 70R, 70L is completely shut state (non transmittable state), the transmittance adjusting unit 71 increases the transmittance of the one of the liquid crystal shutters 70R, 70L by 5% every second.

The transmittance adjusting unit 71 maintains the transmittance of the other one of the liquid crystal shutters 70R, 70L constant (see reference sign T3). Accordingly, when the transmittance of the one of the liquid crystal shutters 70R, 70L is reduced with elapse of the time, the light intensity (light amount) of a visible light entering into the non-dominant eye of subject's eyes E reduces with elapse of the time, and the light intensity of a visible light entering a dominant eye of the subject's eyes E is maintained constant. Consequently, the light intensity difference, which is a difference between light intensities of the visible lights entering respectively into both subject's eyes E, is increased.

Figure 18:
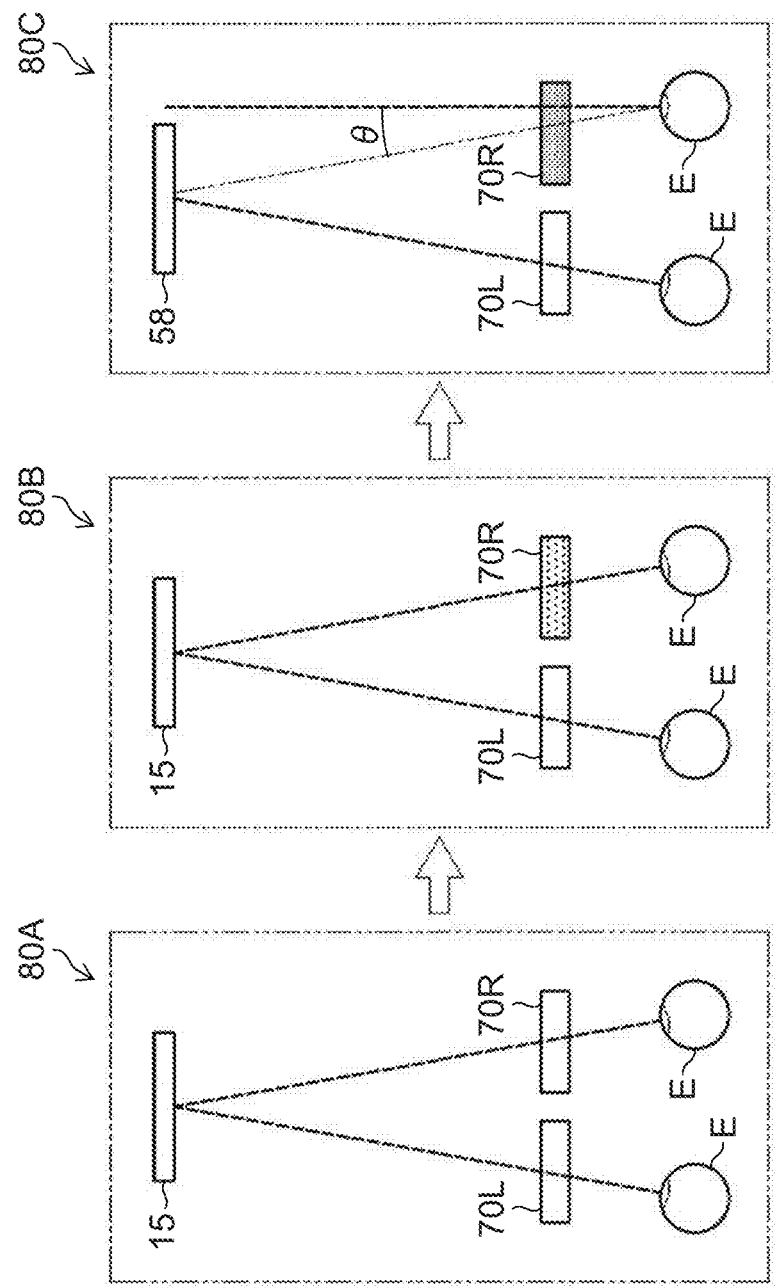
FIG. 18 is an explanatory drawing for explaining a change of a gaze direction of a subject's eye (non-dominant eye) when light intensity difference of a visible lights entering respectively to both subject's eyes.

FIG. 18 is an explanatory drawing for explaining a change of a gaze direction of a subject's eye E (non-dominant eye) when light intensity difference of visible lights entering respectively to both subject's eyes E. As indicated by reference sign 80A in FIG. 18, when the light intensity difference between the visible lights entering respectively into both subject's eyes E is zero (including almost zero), a fusion, which corresponds to images of the visual target 28 viewed respectively with both subject's eyes E and recognized as one image by the subject, is established.

Subsequently, as indicated by reference sign 80B, the transmittance adjusting unit 71 reduces the transmittance of the liquid crystal shutter 70R corresponding to the previously selected non-dominant eye (the right eye here) of subject's eyes E with elapse of the time. In this case, when the light intensity difference described above falls within a fixed range (certain range), the fusion is established.

As indicated by reference sign 80C, when the light intensity difference described above is increased beyond the fixed range, the subject cannot recognize the images of the visual target 28 viewed with both subject's eyes E respectively as one image, and thus the convergence is not maintained and the fusion is broken. Consequently, the eye position (gaze direction) of the non-dominant eye of subject's eyes E changes.

In this case, in the ophthalmologic device 10 of this embodiment, under the control of the general control unit 50, measurement of the wave-front sensors 18R, 18L by the sensor control unit 54 and analysis by the analyzing unit 55 are performed, thereby enabling to measure a change (phoria angle $\theta$) of the eye position of the non-dominant eye in association with the breaking of fusion, and a change of the optical characteristics of the subject's eye E in association with the change of the eye position, specifically, a change of the refractive power (refractive value).

FIG. 19 is a graph showing an example of temporal changes of eye positions and the refractive powers (D) of the subject's eyes E in a case where the light intensity difference of the visible lights entering respectively into both subject's eyes E having phoria-myopia. As indicated by reference sign 81A in FIG. 19, when the change of the eye position of the non-dominant eye occurs in association with the breaking of fusion (indicated by a dotted circle in the drawing), it is possible to measure the phoria angle $\theta$ of the subject's eyes E based on the change of the eye position. Then, as indicated by reference sign 81B in FIG. 19, when the subject's eyes E have phoria-myopia, a change in the refractive powers, that is, an accommodative change, of the subject's eyes E occurs in association with the change of the eye position of the non-dominant eye. Specifically, when the non-dominant eye is displaced outward (laterally), the refractive powers of the subject's eyes E are shifted toward a far vision side (see an arrow in the drawing).

Returning back to FIG. 16, the measurement data indicating temporal change of the eye position and the refractive powers (D) of the subject's eyes E acquired by the wave-front sensors 18R, 18L and the analyzing unit 55 in the prism power determination mode is output to the prism power determining unit 72 from the analyzing unit 55.

When an accommodative change occurs in association with the change of the eye position of the non-dominant eye of subject's eyes E as illustrated in FIG. 19 described above, the prism power determining unit 72 determines the prism powers of the prisms to be added to the subject's eyes E based on the measurement results of the phoria angle $\theta$ and the refractive powers (D) of the subject's eyes E. Note that the method of determining the prism powers is known in the related art and thus detailed description will be omitted. The prism power determining unit 72 outputs the determination result of the prism powers to the output unit 59. The output unit 59 causes the display output unit 60 to display and output the determination result of the prism powers as prescription values and stores the same in the memory 61.

As described above, since the ophthalmologic device 10 of the third embodiment can automatically measure the change of the eye positions (phoria angle $\theta$) and the accommodative change in association with breaking of fusion of subject's eyes E, Step S25 illustrated in FIG. 13 described above can be automated. In other words, each of acquisition of the full correction value, determination of the prism powers and determination of the addition powers can be performed automatically by a single ophthalmologic device 10.

<Others>

When the accommodative amplitudes of both subject's eyes E satisfy the accommodative amplitude criteria described above, the addition power determining unit 58 of the respective embodiments described above determines the addition powers based on values and fluctuations of measurement data of the spherical equivalent power for each addition power acquired by the analyzing unit 55. However, the addition power may be determined by using other methods.

Figure 20:
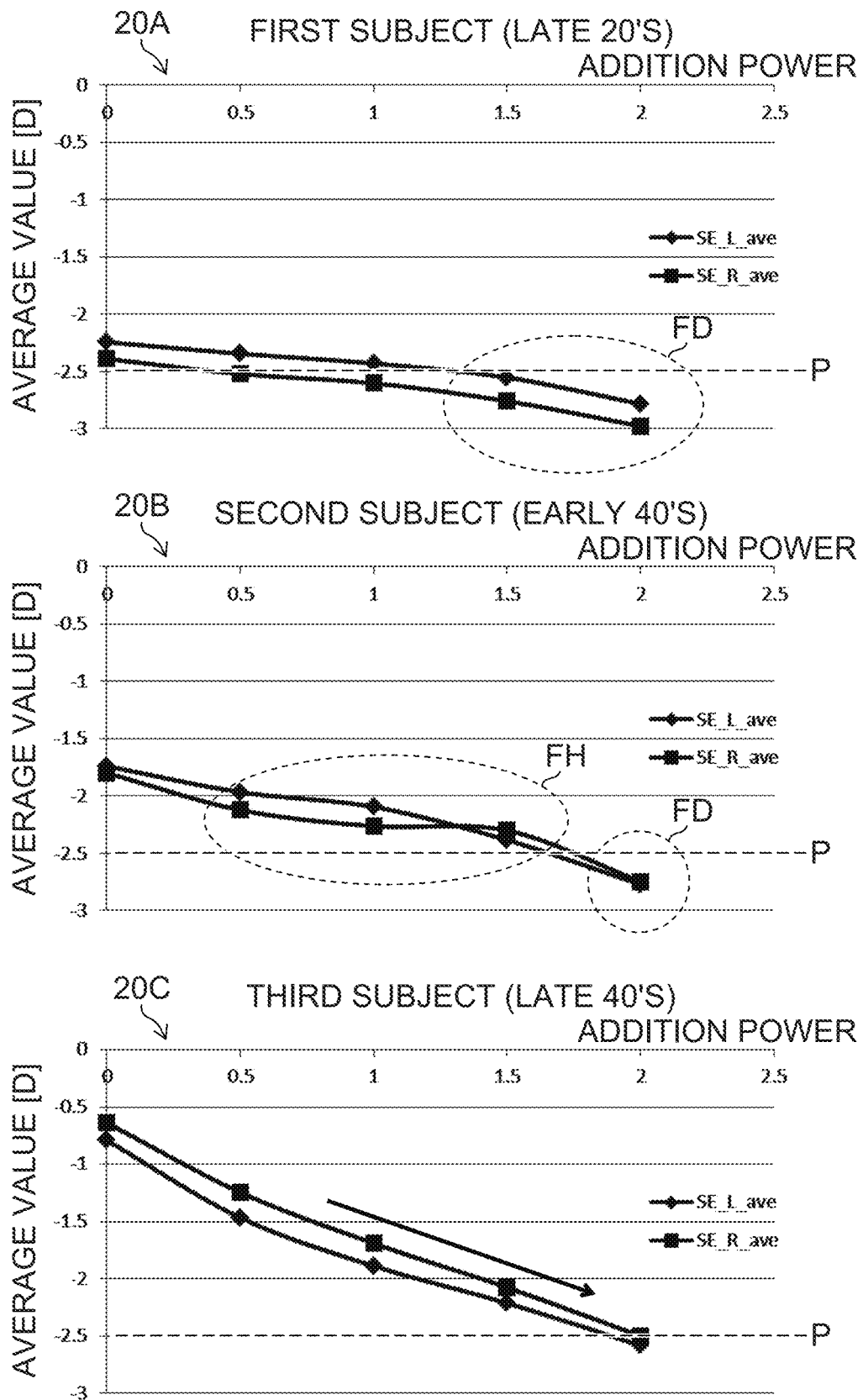
FIG. 20 is an explanatory drawing for explaining another method of determining the power by an addition power determining unit.

FIG. 20 is an explanatory drawing for explaining another method of determining the addition powers by an addition power determining unit 58. As illustrated in FIG. 20, the addition power determining unit 58 calculates an average value of the measurement data of the spherical equivalent power for each addition power acquired by the analyzing unit 55. For example, the addition power determining unit 58 calculates an average values for 3 seconds to 5 seconds after presenting distance change, for each addition power.

As indicated by reference sign 20A, in the case of the first subject described above (see FIG. 10) whose accommodative amplitudes of both subject's eyes E satisfy the accommodative amplitude criteria, the average value of the measurement data of the spherical equivalent power is almost constant in a range of the addition power up to 1.0 D, while the average value of the measurement data of the spherical equivalent power decreases gradually at the addition power of 1.5 D and the addition power of 2.0 D (see reference sign FD in the drawing).

As indicated by reference sign 20B, in the case of the second subject described above (see FIG. 11) whose accommodative amplitudes of both subject's eyes E satisfy the accommodative amplitude criteria, the average value of the measurement data of the spherical equivalent power is almost constant (see reference sign FH) in a range of the addition power from 0.5 D to 1.5 D, while the average value of the measurement data of the spherical equivalent power decreases at the addition power of 2.0 D (see reference sign FD in the drawing).

In contrast, as indicated by reference sign 20C, in the case of the third subject (see FIG. 12) described above whose accommodative amplitudes of both subject's eyes E do not satisfy the accommodative amplitude criteria, the average value of the measurement data of spherical equivalent power decreases linearly in association with the increase of the addition power as indicated by an arrow in the drawing.

In this manner, the present inventors have found that, when the accommodative amplitudes of both subject's eyes E satisfy the accommodative amplitude criteria, that is, when the accommodative amplitudes remain in both eyes, a constant part in which the average value is substantially constant and a decreasing part in which the average value decreases continuously appear in the waveform of the average value of the measurement data of the spherical equivalent power for each addition power. The present inventors have also found that the addition powers corresponding to the constant part described above (a region of the constant part on a boundary side between the decreasing part and the constant part) are respectively suitable for addition powers of both subject's eyes E. Therefore, the addition power determining unit 58 can determine addition powers suitable for both subject's eyes E by respectively acquiring average value of the measurement data of the spherical equivalent power for each addition power and analyzing the change of the average values with respect to the addition power.

In the respective embodiments described above, the wave-front sensors 18R, 18L are used as means for acquiring the various ocular characteristics described above of both subject's eyes E viewing (naturally) the visual target 28. However, instead of the wave-front sensors, it is possible to use various known devices (ocular characteristic acquiring units) capable of acquiring at least the optical characteristics of both eyes. In addition, the ophthalmologic device 10 of this embodiment may be configured to perform at least only determination of the addition powers, and acquisition or determination of other full correction values and prism powers may be performed by separate devices.

In the respective embodiments described above, the presenting distance of the visual target 28 from the far vision distance to the near vision distance is changed in a short time by driving the visual target moving mechanism 16 at a high speed so as to acquire the state of convergence accommodation of the subject's eyes E which react rapidly. However, the change (switching) of the presenting distance in a short time may be performed with other methods.

Figure 21:
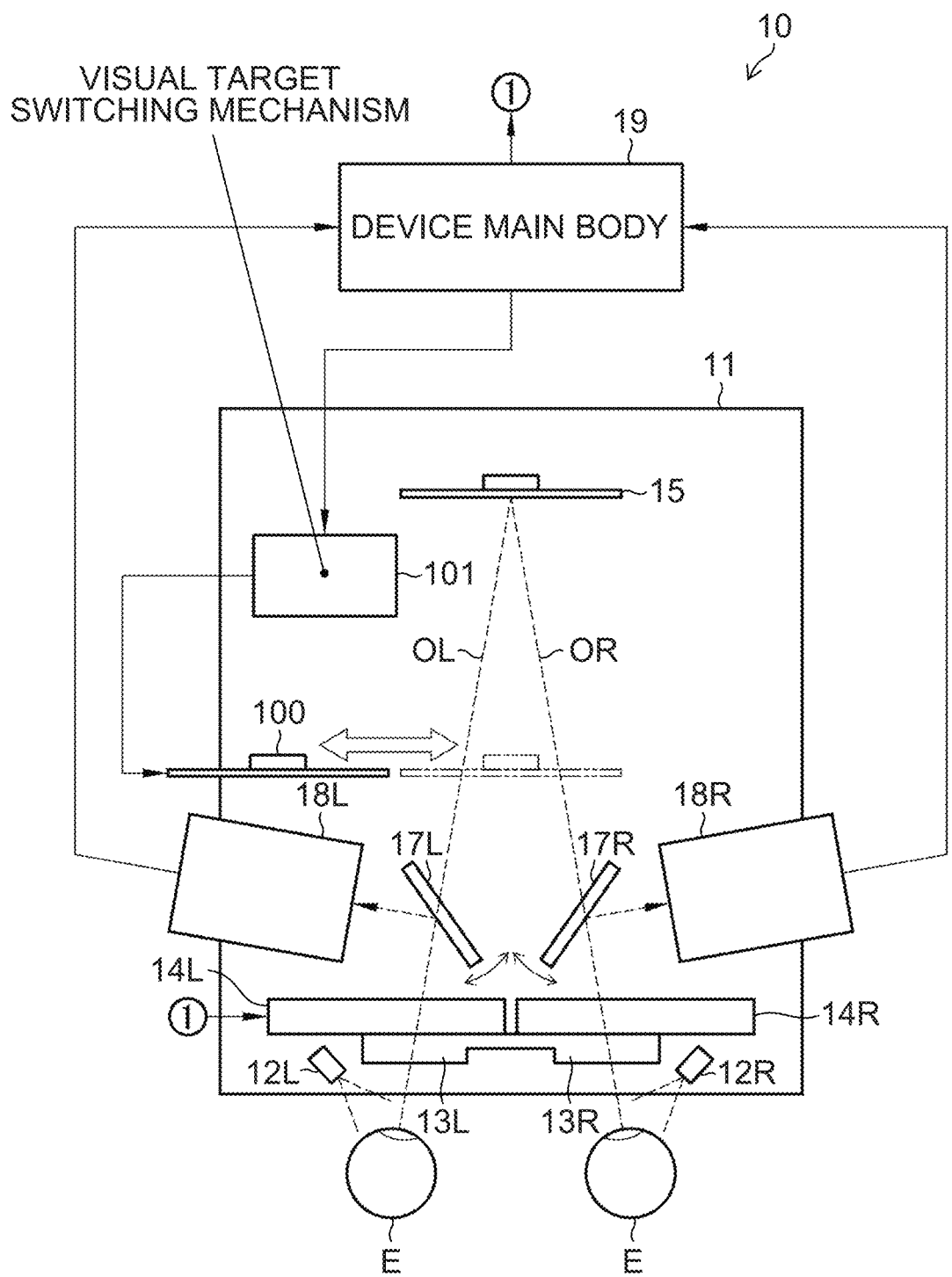
FIG. 21 is an explanatory drawing for explaining Modified Example 1 of changing the presenting distance of the visual target.
Figure 22:
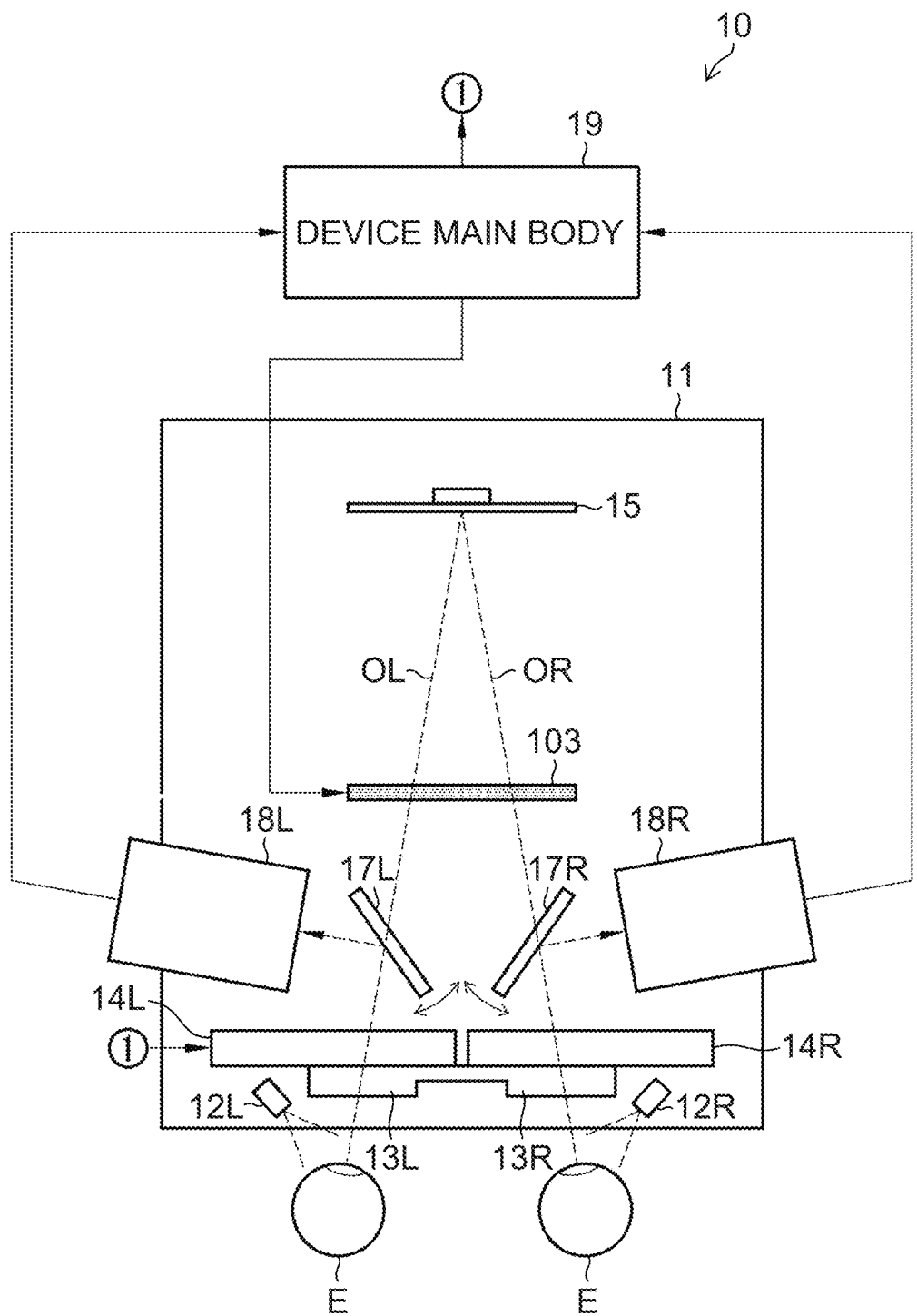
FIG. 22 is an explanatory drawing for explaining Modified Example 2 of changing the presenting distance of the visual target.

FIG. 21 is an explanatory drawing for explaining Modified Example 1 of changing the presenting distance of the visual target. Further, FIG. 22 is an explanatory drawing for explaining Modified Example 2 of changing the presenting distance of the visual target. Note that the respective modified examples illustrated in FIG. 21 and FIG. 22 are basically the same as the first embodiment described above other than the configuration relating to the change of the presenting distance, those having the same function and configuration as the first embodiment are designated by the same reference numerals and descriptions thereof are omitted.

Modified Example 1

As illustrated in FIG. 21, in the Modified Example 1, the visual target 28 for far vision (see upper part in FIG. 4) is displayed with the visual target presenting unit 15 fixed at a position corresponding to the far vision distance described above. In Modified Example 1, a visual target presenting unit 100 and a visual target switching mechanism 101 (which corresponds to the presenting distance changing unit of the present invention) are provided separately instead of the guide rail 25, the supporting unit 26, and visual target moving unit 27 describe above (see FIG. 1).

The visual target presenting unit 100 is basically the same as the visual target presenting unit 15, and displays the visual target 28 for near vision (see lower part of FIG. 4). The visual target presenting unit 100 is held by the visual target switching mechanism 101 so as to be movable between a presenting position (indicated by dotted line) in front of the subject's eyes E and corresponding to the near vision distance described above, and a retracted position (indicated by a solid line) retracted sideward (any of up, down, left and right) from the presenting position. Further, the visual target presenting unit 100 may be configured to be fallen on the table 11 (tilt-down state) so as to retreat when viewed by far vision, and to stand upright (a stand-up state) to present the visual target 28 for near vision when viewed by near vision.

The visual target switching mechanism 101, although illustration is omitted, includes: a holding unit such as a guide rail for slidably holding the visual target presenting unit 100 between the presenting position and the retracted position; and a driving mechanism such as a motor for providing the visual target presenting unit 100 with a drive force. Driving of the visual target switching mechanism 101 is controlled by the visual target movement control unit 52 (see FIG. 6).

When the visual target switching mechanism 101 moves the visual target presenting unit 100 to the retracted position under the control of the visual target movement control unit 52, the visual target 28 of the visual target presenting unit 15 is presented to subject's eyes E. In contrast, when the visual target switching mechanism 101 moves the visual target presenting unit 100 to the presenting position, the visual target 28 of the visual target presenting unit 100 is presented to subject's eyes E. Therefore, by moving the visual target presenting unit 100 from the retracted position to the presenting position in a short time by the visual target switching mechanism 101, the presenting distance of the visual target 28 can be switched from the far vision distance to the near vision distance in a short time as in the first embodiment.

At this time, the distance of moving the visual target presenting unit 100 from the retracted position to the presenting position can be made much shorter than the distance to move the visual target presenting unit 15 from the far vision distance to the near vision distance according to the first embodiment. Therefore, in Modified Example 1, it is possible to switch the presenting distance of the visual target 28 in a shorter time than the first embodiment. Consequently, it is possible to more reliably acquire the state of the convergence accommodation of subject's eyes E that react rapidly.

Note that in Modified Example 1, the visual target presenting unit 100 is moved automatically between the retracted position and the presenting position by the visual target switching mechanism 101. However, movement of the visual target presenting unit 100 may be performed by manual operation.

Modified Example 2

As illustrated in FIG. 22, Modified Example 2 is the same as Modified Example 1 described above in that the visual target presenting unit 15 is fixed to a position corresponding to the far vision distance to display the visual target 28 for far vision, but includes a visual target presenting unit 103 different from that in Modified Example 1 is provided.

The visual target presenting unit 103 is provided in front of the subject's eyes E at a presenting position corresponding to the near vision distance described above. As the visual target presenting unit 103, for example, a transmissive liquid crystal display or a transparent (transmissive) display such as a heads-up display may be used. The visual target presenting unit 103 is switched between a display state in which the visual target 28 for near vision is displayed and a non-display state in which the visual target 28 is not displayed under the control of the general control unit 50 describe above. In this case, the visual target presenting unit 103 and the general control unit 50 function as the presenting distance changing unit of the present invention. Note that the visual target presenting unit 103 becomes a light-shielded state in which subject's eyes E cannot visibly recognize the visual target presenting unit 15 when switched into the display state.

When the visual target presenting unit 103 is switched to the non-display state, the subject's eyes E can visually recognize the visual target 28 displayed on the visual target presenting unit 15 with both eyes through the visual target presenting unit 103. Accordingly, the visual target 28 for far vision is presented for both subject's eyes E. In contrast, when the visual target presenting unit 103 is switched to the display state, the subject's eyes E can visually recognize the visual target 28 displayed on the visual target presenting unit 103 with both eyes. Accordingly, the visual target 28 for near vision is presented for both subject's eyes E. Therefore, by switching the visual target presenting unit 103 from the non-display state to the display state, the presenting distance of the visual target 28 can be switched from the far vision distance to the near vision distance as in the first embodiment.

At this time, in Modified Example 2, the presenting distance of the visual target 28 can be switched from the far vision distance to the near vision distance without moving the visual target presenting unit 103 at all, and thus the presenting distance of the visual target 28 can be switched in a shorter time than the first embodiment and Modified Example 1. Consequently, it is possible to more reliably acquire the state of the convergence accommodation of subject's eyes E that react rapidly.

Note that the method of switching the presenting distance of the visual target 28 from the far vision distance to the near vision distance is not limited to those in the embodiments, Modified Example 1, and Modified Example 2 described above, and various methods that allows changing of the presenting distance of the visual target 28 are used.

In the respective embodiments described above, the visual target 28 which are presented by the visual target presenting unit 15 or the like, that is, an external fixation visual target is used. However, it may be configured to use an internal fixation visual target that displays commonly (the same) or separately a visual target to be viewed with both eyes but can be recognized as one image by fusion. It also may be configured to use a visual target which can be presented optically at a distance of 5 m may be used as the visual target 28 for far vision.

In the respective embodiments described above, the change of the ocular characteristics (optical characteristics or the like) of subject's eyes E is continuously measured for a fixed time before and after the change of the presenting distance of the visual target 28 from the far vision distance to the near vision distance. However, it may be configured to continuously measure the changes of the ocular characteristics for a fixed time after the change of the presenting distance.

In the respective embodiments described above, the changes of the ocular characteristics (optical characteristics or the like) of both subject's eyes E are measured simultaneously. However, measurement of the changes of the ocular characteristics may be performed for each eye if the visual target 28 is presented simultaneously to both subject's eyes E.

In the respective embodiments described above, changes of the spherical equivalent power (equivalent refractive power) or the like are measured as measurement of the changes of the optical characteristics of both subject's eyes E in association with the change of the presenting distance of the visual target 28. However, it may be configured to measure changes of the spherical aberration and other optical characteristics such as high-order aberrations.

In the respective embodiments described above, the addition powers suitable for subject's eyes E are determined by performing the above-described near vision dynamic measurement repeatedly for each addition power to be added to the both subject's eyes E. However, the present invention is not limited thereto. For example, if a typical profile of change in optical characteristics can be obtained as the measurement result of the near vision dynamic measurement at an arbitrary addition power added to both subject's eyes E for the first time, the near vision dynamic measurement may be completed at one time and the addition powers may be determined.

In the respective embodiments described above, operations up to determination of the addition powers (output of the prescription values) are performed automatically by the ophthalmologic device 10. However, the present invention may also be applied also in aa case where operations up to the acquisition of the ocular characteristics (optical characteristics or the like) of both subject's eyes E for each addition power are performed by the ophthalmologic device 10, and then, determination of the addition powers are performed by the examiner or the like, in the method of manufacturing the spectacle lenses (manufacturing process).

REFERENCE SIGNS LIST

10 . . . ophthalmologic device
11 . . . table
12R, 12L . . . infrared source
13R, 13L . . . eyepiece
14R, 14L . . . addition power adding unit
15, 100, 103 . . . visual target presenting unit
16 . . . visual target moving mechanism
17R, 17L, 31 . . . dichroic mirror
18R, 18L . . . wave-front sensor
19 . . . device main body
21R, 21L . . . turret
22 . . . lens
23R, 24R . . . rotary driving unit
25 . . . guide rail
26 . . . supporting unit
27 . . . visual target moving unit
28 . . . visual target
29A . . . anterior eye part observation system
29B . . . aberration measurement system
30 . . . objective lens
34 . . . alignment optical system
35A, 35B . . . relay lens
36 . . . imaging lens
37, 46 . . . image sensor
41 . . . collimator lens
42 . . . beam splitter
43 . . . mirror
44A, 44B . . . lens system
45 . . . Hartmann plate
50 . . . general control unit
51 . . . operating unit
52 . . . visual target movement control unit
53 . . . power change control unit
54 . . . sensor control unit
55 . . . analyzing unit
56 . . . fully corrected state confirming unit
57 . . . accommodative amplitude judging unit
58 . . . addition power determining unit
59 . . . output unit
60 . . . display output unit
61 . . . memory
70R, 70L . . . liquid crystal shutter
71 . . . transmittance adjusting unit
72 . . . prism power determining unit
101 . . . visual target switching mechanism

The invention claimed is:

1. An ophthalmologic device comprising:
a visual target presenting unit configured to present a common visual target to be viewed with both subject's eyes;
a presenting distance changing unit configured to change a presenting distance of the visual target presented by the visual target presenting unit from a predetermined far vision distance to a predetermined near vision distance;
an ocular characteristic acquiring unit configured to objectively acquire an optical characteristic of the subject's eyes, optical characteristics of both subject's eyes being simultaneously acquired, or the optical characteristics being acquired for each of the subject's eyes;
an addition power adding unit configured to add the addition power to the both subject's eyes; and
a control unit configured to cause the presenting distance changing unit to change the presenting distance and the ocular characteristic acquiring unit to continuously acquire the optical characteristic, in a state in which an arbitrary addition power is added to the both subject's eyes by the addition power adding unit, and cause the ocular characteristic acquiring unit to acquire a change in the optical characteristic for a fixed time before and after the presenting distance of the visual target is changed by the presenting distance changing unit, the fixed time being shorter than a time from a presentation of convergence stimulation for the subject's eyes until the subject's eyes start convergence accommodation.

2. The ophthalmologic device according to claim 1, wherein
the addition power adding unit changes the addition power to be added to the both subject's eyes, and
the control unit performs repeating control that causes the presenting distance changing unit to change the presenting distance and causes the ocular characteristic acquiring unit to continuously acquire the optical characteristic, every time when the addition power adding unit changes the addition power to be added to the both subject's eyes.

3. The ophthalmologic device according to claim 2, comprising an addition power determining unit configured to determine the addition power suitable to the both subject's eyes based on a result of acquisition of the optical characteristic for each addition power acquired by the ocular characteristic acquiring unit, by the repeating control.

4. The ophthalmologic device according to claim 3, comprising an accommodative amplitude judging unit configured to judge an accommodative amplitude of the subject's eyes based on the optical characteristic acquired by the ocular characteristic acquiring unit, wherein
when the accommodative amplitude judged by the accommodative amplitude judging unit satisfies a predetermined accommodative amplitude criteria, the addition power determining unit determines the addition power based on judgment result of value and fluctuation of the optical characteristic for each addition power, which have been acquired by the ocular characteristic acquiring unit.

5. The ophthalmologic device according to claim 3, comprising an accommodative amplitude judging unit configured to judge an accommodative amplitude of the subject's eyes based on the optical characteristic acquired by the ocular characteristic acquiring unit, wherein
when the accommodative amplitude judged by the accommodative amplitude judging unit does not satisfy a predetermined accommodative amplitude criteria and when the optical characteristic acquired by the ocular characteristic acquiring unit shows a return of the optical characteristic indicating that the optical characteristic gets closer according to the elapse of the time, to a value before the presenting distance is changed, the addition power determining unit determines the addition power based on judgment result of a magnitude of the return for each addition power.

6. The ophthalmologic device according to claim 2, wherein the addition power adding unit determines addition powers to be added to the both subject's eyes in the repeating control, based on the optical characteristic acquired by the ocular characteristic acquiring unit in a state in which no addition power is added to the both subject's eyes.

7. The ophthalmologic device according to claim 1, comprising a fully corrected state confirming unit configured to objectively confirm a fully corrected state of the both subject's eyes based on the optical characteristic acquired by the ocular characteristic acquiring unit when the presenting distance is the far vision distance.

8. The ophthalmologic device according to claim 1, wherein the ocular characteristic acquiring unit acquires a spherical equivalent power as the optical characteristic.

9. The ophthalmologic device according to claim 1, wherein the ocular characteristic acquiring unit acquires the optical characteristic and convergence angles of the both subject's eyes.

10. The ophthalmologic device according to claim 1, wherein the ocular characteristic acquiring unit comprises:
   a pair of optical members individually provided for optical paths connecting the both subject's eyes and the visual target; and
   a pair of wave-front sensors provided respectively at positions shifted in the vertical direction with respect to the optical paths from positions of the optical members, the pair of wave-front sensors configured to respectively emit measuring lights toward the optical members facing the wave-front sensors, wherein
   the pair of optical members respectively transmit image lights of the visual target, reflect measuring lights entering from the wave-front sensors to the subject's eyes facing the optical members, and reflect the measuring lights reflected from the subject's eyes toward the wave-front sensors facing the optical members,
   the pair of wave-front sensors respectively receive the measuring lights entering from the optical members facing the wave-front sensors and output light receiving signals, and
   the ocular characteristic acquiring unit acquires the optical characteristic based on t light receiving signals output from the wave-front sensors.

11. A method of operating an ophthalmologic device comprising:
   a visual target presenting step of presenting a common visual target to be viewed with both subject's eyes;
   a presenting distance changing step of changing a presenting distance of the visual target presented in the visual target presenting step from a predetermined far vision distance to a predetermined near vision distance;
   an ocular characteristic acquiring step of objectively acquiring an optical characteristic of the subject's eyes, optical characteristics of both subject's eyes being simultaneously acquired, or the optical characteristics being acquired for each of the subject's eyes;
   an addition power adding step of adding the addition power to the both subject's eyes; and
   a controlling step of performing the change of the presenting distance by the presenting distance changing step and the continuous acquisition of the optical characteristic by the ocular characteristic acquiring step, in a state in which the addition power is added to the both subject's eyes in the addition power adding step, and acquiring a change in the optical characteristic for a fixed time before and after the presenting distance of the visual target is changed, the fixed time being shorter than a time from a presentation of convergence stimulation for the subject's eyes until the subject's eyes start convergence accommodation.

12. The method of operating an ophthalmologic device according to claim 11, wherein
   the addition power to be added to the both subject's eyes is changed in the addition power adding step, and
   the controlling step performs repeating control for repeatedly performing the change of the presenting distance by the presenting distance changing step and continuous acquisition of the optical characteristic by the ocular characteristic acquiring step, every time when the addition power to be added to the both subject's eyes is changed in the addition power adding step.

13. The method of operating an ophthalmologic device according to claim 12, comprising an addition power determining step of determining the addition power suitable to the both subject's eyes based on a result of acquisition of the optical characteristic acquired for each addition power by the repeating control.

14. The method of operating an ophthalmologic device according to claim 11, comprising a fully corrected state confirming step of objectively confirming a fully corrected state of the both subject's eyes based on the optical characteristic acquired in the ocular characteristic acquiring step when the presenting distance is the far vision distance.

15. An ophthalmologic device comprising:
   a display configured to present a common visual target to be viewed with both subject's eyes;
   a sliding support configured to change a presenting distance of the visual target presented by the display from a predetermined far vision distance to a predetermined near vision distance;
   a wave-front sensor configured to objectively acquire an optical characteristic of the subject's eyes, optical characteristics of both subject's eyes being simultaneously acquired, or the optical characteristics being acquired for each of the subject's eyes;
   a plurality of lenses configured to add an addition power to the both subject's eyes; and
   processing circuitry configured to cause the sliding support, to change the presenting distance and the wave-front sensor to continuously acquire the optical characteristic, in a state in which an arbitrary addition power is added to the both subject's eyes by the plurality of lenses, and cause the ocular characteristic acquiring unit to acquire a change in the optical characteristic for a fixed time before and after the presenting distance of the visual target is changed by the presenting distance changing unit, the fixed time being shorter than a time from a presentation of convergence stimulation for the subject's eyes until the subject's eyes start convergence accommodation.

\* \* \* \* \*